US011564683B2

(12) United States Patent
Vendely et al.

(10) Patent No.: US 11,564,683 B2
(45) Date of Patent: Jan. 31, 2023

(54) APPARATUS AND METHOD TO APPLY BUTTRESS TO END EFFECTOR OF SURGICAL STAPLER VIA DRIVEN MEMBER

(71) Applicant: Ethicon LLC, Guaynabo, PR (US)

(72) Inventors: Michael J. Vendely, Lebanon, OH (US); Mark S. Zeiner, Mason, OH (US); Heather Strang, West Chester, OH (US); Pamela M. Ridgley, Lebanon, OH (US); Christopher A. Denzinger, Cincinnati, OH (US); Christopher Q. Seow, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/022,209

(22) Filed: Sep. 16, 2020

(65) Prior Publication Data

US 2022/0079580 A1 Mar. 17, 2022

(51) Int. Cl.
*A61B 17/072* (2006.01)
*A61B 17/068* (2006.01)

(52) U.S. Cl.
CPC ........ *A61B 17/0686* (2013.01); *A61B 17/072* (2013.01); *A61B 2017/07264* (2013.01);
(Continued)

(58) Field of Classification Search
CPC . A61B 17/07292; A61B 17/08; A61B 17/105; A61B 17/072; A61B 2017/081
(Continued)

(56) References Cited

U.S. PATENT DOCUMENTS 4,930,674 A 6/1990 Barak
5,358,510 A 10/1994 Luscombe et al.
(Continued)

FOREIGN PATENT DOCUMENTS

EP 2 090 248 A2 8/2009
EP 3 072 460 A2 9/2016
(Continued)

OTHER PUBLICATIONS

Gore Seamguard Bioabsorbable Staple Line Reinforcement, Configured for Endoscopic Surgical Staplers, Instructions for Use, Jun. 2019, 136 pgs.
(Continued)

*Primary Examiner* — Gloria R Weeks
(74) *Attorney, Agent, or Firm* — Frost Brown Todd LLP

(57) ABSTRACT

An apparatus is configured to apply an adjunct material to at least one of a first stapling surface or a second stapling surface of a surgical stapler. The apparatus includes a contact structure defining a longitudinal axis and an expansion mechanism. The contact structure includes a first contact member configured to support a first portion of the adjunct material and a second contact member movably coupled with the first contact member that is configured to support a second portion of the adjunct material. The first and second contact members are configured to move away from one another in opposing directions to apply the first portion of the adjunct material to the first stapling surface and the second portion of the adjunct material to the second stapling surface. The expansion mechanism is selectively operable to transition the contact structure from a non-expanded state toward the expanded state.

20 Claims, 30 Drawing Sheets

(52) U.S. Cl.
CPC .............. *A61B 2017/07271* (2013.01); *A61B 2217/007* (2013.01)

(58) Field of Classification Search
USPC ...................................................... 606/151
See application file for complete search history.

(56) References Cited

U.S. PATENT DOCUMENTS

| | | | |
|---|---|---|---|
| 5,372,868 A | 12/1994 | Prewo et al. | |
| 5,655,698 A | 8/1997 | Yoon | |
| 5,697,542 A | 12/1997 | Knodel et al. | |
| 5,752,965 A | 5/1998 | Francis et al. | |
| 5,769,892 A | 6/1998 | Kingwell | |
| 5,810,855 A | 9/1998 | Rayburn et al. | |
| 5,833,695 A | 11/1998 | Yoon | |
| 5,901,895 A | 5/1999 | Heaton et al. | |
| 5,902,312 A | 5/1999 | Frater et al. | |
| 6,019,791 A | 2/2000 | Wood | |
| 6,099,551 A | 8/2000 | Gabbay | |
| 6,273,897 B1 | 8/2001 | Dalessandro et al. | |
| 6,325,810 B1 | 12/2001 | Hamilton et al. | |
| 6,592,597 B2 | 7/2003 | Grant et al. | |
| 6,638,285 B2 | 10/2003 | Gabbay | |
| 7,147,138 B2 | 12/2006 | Shelton, IV | |
| 7,377,928 B2 | 5/2008 | Zubik et al. | |
| 7,380,696 B2 | 6/2008 | Shelton, IV et al. | |
| 7,559,937 B2 | 7/2009 | De La Torre et al. | |
| 7,665,646 B2 | 2/2010 | Prommersberger | |
| 7,708,180 B2 | 5/2010 | Murray et al. | |
| 7,845,533 B2 | 12/2010 | Marczyk et al. | |
| 8,052,697 B2 | 11/2011 | Phillips | |
| 8,210,411 B2 | 7/2012 | Yates et al. | |
| 8,317,790 B2 | 11/2012 | Bell et al. | |
| 8,348,130 B2 | 1/2013 | Shah et al. | |
| 8,408,439 B2 | 4/2013 | Huang et al. | |
| 8,453,904 B2* | 6/2013 | Eskaros | A61B 17/072 227/181.1 |
| 8,453,914 B2 | 6/2013 | Laurent et al. | |
| 8,464,925 B2 | 6/2013 | Hull et al. | |
| 8,864,009 B2 | 10/2014 | Shelton, IV et al. | |
| 8,920,444 B2* | 12/2014 | Hiles | A61B 17/0643 227/176.1 |
| 9,186,142 B2 | 11/2015 | Fanelli et al. | |
| 9,211,120 B2 | 12/2015 | Scheib et al. | |
| 9,220,501 B2 | 12/2015 | Baxter, III et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,833,238 B2 | 12/2017 | Baxter, III et al. | |
| 9,839,421 B2 | 12/2017 | Zerkle et al. | |
| 9,999,408 B2 | 6/2018 | Boudreaux et al. | |
| 10,092,292 B2 | 10/2018 | Boudreaux et al. | |
| 10,166,023 B2 | 1/2019 | Vendely et al. | |
| 10,213,198 B2 | 2/2019 | Aronhalt et al. | |
| 10,349,939 B2 | 7/2019 | Shelton, IV et al. | |
| 10,869,663 B2* | 12/2020 | Shelton, IV | A61B 17/07292 |
| 10,932,779 B2 | 3/2021 | Vendely et al. | |
| 10,993,716 B2 | 5/2021 | Shelton, IV et al. | |
| 11,033,269 B2 | 6/2021 | Vendely et al. | |
| 11,045,196 B2 | 6/2021 | Olson et al. | |
| 11,051,812 B2 | 7/2021 | Hopkins et al. | |
| 11,058,418 B2 | 7/2021 | Shelton, IV et al. | |
| 11,065,000 B2 | 7/2021 | Shankarsetty et al. | |
| 11,413,040 B2 | 8/2022 | Zeiner et al. | |
| 11,419,605 B2 | 8/2022 | Denzinger et al. | |
| 2005/0070929 A1* | 3/2005 | Dalessandro | A61B 17/07292 606/151 |
| 2005/0267325 A1 | 12/2005 | Bouchier et al. | |
| 2006/0173470 A1 | 8/2006 | Oray et al. | |
| 2007/0162056 A1 | 7/2007 | Gerbi et al. | |
| 2007/0179528 A1 | 8/2007 | Soltz et al. | |
| 2007/0246505 A1 | 10/2007 | Pace-Floridia et al. | |
| 2008/0128469 A1 | 6/2008 | Dalessandro et al. | |
| 2008/0169329 A1 | 7/2008 | Shelton et al. | |
| 2008/0203134 A1 | 8/2008 | Shah et al. | |
| 2009/0001122 A1 | 1/2009 | Prommersberger et al. | |
| 2009/0084825 A1 | 4/2009 | Larson | |
| 2009/0206126 A1 | 8/2009 | Huitema et al. | |
| 2010/0087840 A1 | 4/2010 | Ebersole et al. | |
| 2010/0163598 A1 | 7/2010 | Belzer | |
| 2011/0017802 A1 | 1/2011 | Ma et al. | |
| 2011/0087279 A1 | 4/2011 | Shah et al. | |
| 2011/0248064 A1 | 10/2011 | Marczyk | |
| 2012/0018487 A1 | 1/2012 | Bettuchi et al. | |
| 2012/0080336 A1 | 4/2012 | Shelton, IV et al. | |
| 2012/0265154 A1 | 10/2012 | Criscuolo et al. | |
| 2013/0037596 A1 | 2/2013 | Bear et al. | |
| 2013/0075447 A1 | 3/2013 | Weisenburgh, II et al. | |
| 2013/0146642 A1 | 6/2013 | Shelton, IV et al. | |
| 2013/0256378 A1 | 10/2013 | Schmid et al. | |
| 2014/0058194 A1 | 2/2014 | Soletti et al. | |
| 2014/0131418 A1 | 5/2014 | Kostrzewski | |
| 2014/0131419 A1 | 5/2014 | Bettuchi | |
| 2014/0158741 A1 | 6/2014 | Woodard, Jr. et al. | |
| 2014/0239036 A1 | 8/2014 | Zerkle et al. | |
| 2014/0288386 A1 | 9/2014 | Zand et al. | |
| 2014/0291379 A1 | 10/2014 | Schellin et al. | |
| 2015/0041168 A1 | 2/2015 | Dostinov | |
| 2015/0076212 A1 | 3/2015 | Shelton, IV | |
| 2015/0305743 A1* | 10/2015 | Casasanta | A61B 17/068 227/176.1 |
| 2015/0351761 A1 | 12/2015 | Shelton, IV et al. | |
| 2017/0055980 A1 | 3/2017 | Vendely et al. | |
| 2017/0056016 A1 | 3/2017 | Barton et al. | |
| 2017/0056018 A1 | 3/2017 | Zeiner et al. | |
| 2017/0281181 A1 | 10/2017 | Matonick et al. | |
| 2017/0303952 A1 | 10/2017 | Nativ et al. | |
| 2018/0235617 A1 | 8/2018 | Shelton, IV et al. | |
| 2018/0235626 A1 | 8/2018 | Shelton, IV et al. | |
| 2019/0321044 A1 | 10/2019 | Franklin, Sr. | |
| 2020/0015817 A1 | 1/2020 | Harris et al. | |
| 2020/0205823 A1 | 7/2020 | Vendely et al. | |
| 2020/0205825 A1 | 7/2020 | Vendely et al. | |
| 2020/0261080 A1 | 8/2020 | Bakos et al. | |
| 2020/0405436 A1 | 12/2020 | Shelton, IV et al. | |
| 2022/0079581 A1 | 3/2022 | Zeiner et al. | |
| 2022/0079587 A1 | 3/2022 | Zeiner et al. | |
| 2022/0079592 A1 | 3/2022 | Bakos et al. | |
| 2022/0079593 A1 | 3/2022 | Bakos et al. | |

FOREIGN PATENT DOCUMENTS

| | | |
|---|---|---|
| EP | 3 632 342 A2 | 4/2020 |
| EP | 3 673 831 A2 | 7/2020 |

OTHER PUBLICATIONS

International Search Report and Written Opinion dated Nov. 30, 2021 for Application No. PCT/IB2021/058337, 16 pgs.
International Search Report and Written Opinion dated Nov. 29, 2021 for Application No. PCT/IB2021/058165, 14 pgs.
International Search Report and Written Opinion dated Dec. 2, 2021 for Application No. PCT/IB2021/058414, 14 pgs.
International Search Report and Written Opinion dated Feb. 16, 2022 for Application No. PCT/IB2021/060163, 15 pgs.
International Search Report and Written Opinion dated Nov. 30, 2021 for Application No. PCT/IB2021/058396, 14 pgs.
International Search Report and Written Opinion dated Dec. 2, 2021 for Application No. PCT/IB2021/058412, 15 pgs.
International Search Report and Written Opinion dated Nov. 25, 2021 for Application No. PCT/IB2021/058400, 15 pgs.
U.S. Appl. No. 17/022,186.
U.S. Appl. No. 17/022,214.
U.S. Appl. No. 17/022,414.
U.S. Appl. No. 17/022,419.
U.S. Appl. No. 17/022,442; and.
U.S. Appl. No. 17/022,520.

(56) References Cited

OTHER PUBLICATIONS

U.S. Appl. No. 17/022,186, entitled "Apparatus and Method to Apply Buttress to End Effector of Surgical Stapler via Fixed Base," filed Sep. 16, 2020.
U.S. Appl. No. 17/022,214, entitled "Apparatus and Method to Apply Buttresses Separately to Jaws of End Effector of Surgical Stapler," filed Sep. 16, 2020.
U.S. Appl. No. 17/022,414, entitled "Apparatus and Method to Close End Effector of Surgical Stapler onto Buttress," filed Sep. 16, 2020.
U.S. Appl. No. 17/022,419, entitled "Apparatus and Method to Detect Full Seating of Buttress Applicator in End Effector of Surgical Stapler," filed Sep. 16, 2020.
U.S. Appl. No. 17/022,442, entitled "Apparatus and Method to Apply Buttress to End Effector of Surgical Stapler with Authentication," filed Sep. 16, 2020.
U.S. Appl. No. 17/022,520, entitled "Method of Applying Buttress to End Effector of Surgical Stapler," filed Sep. 16, 2020.

\* cited by examiner

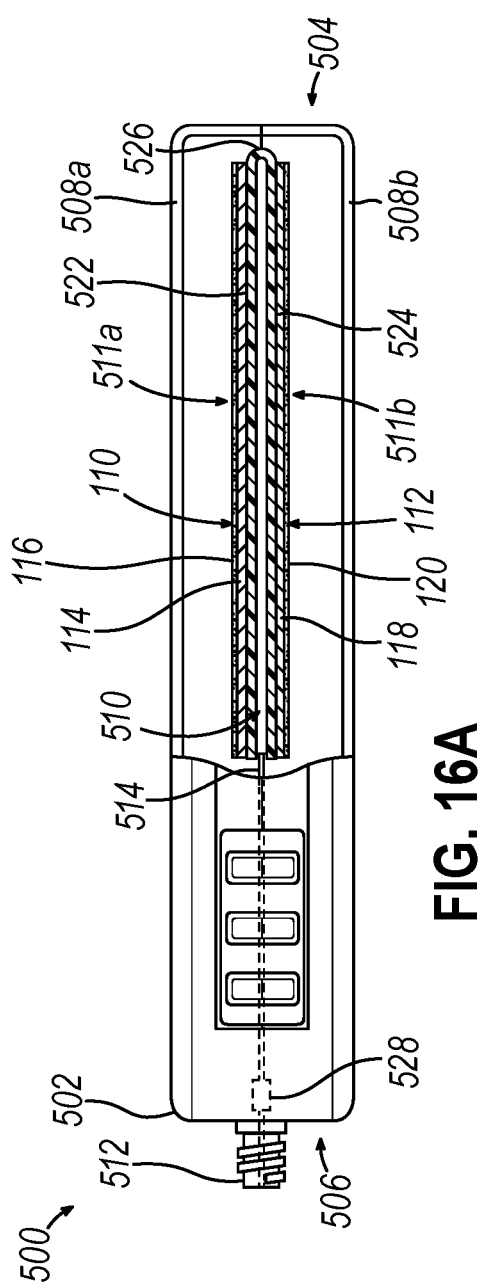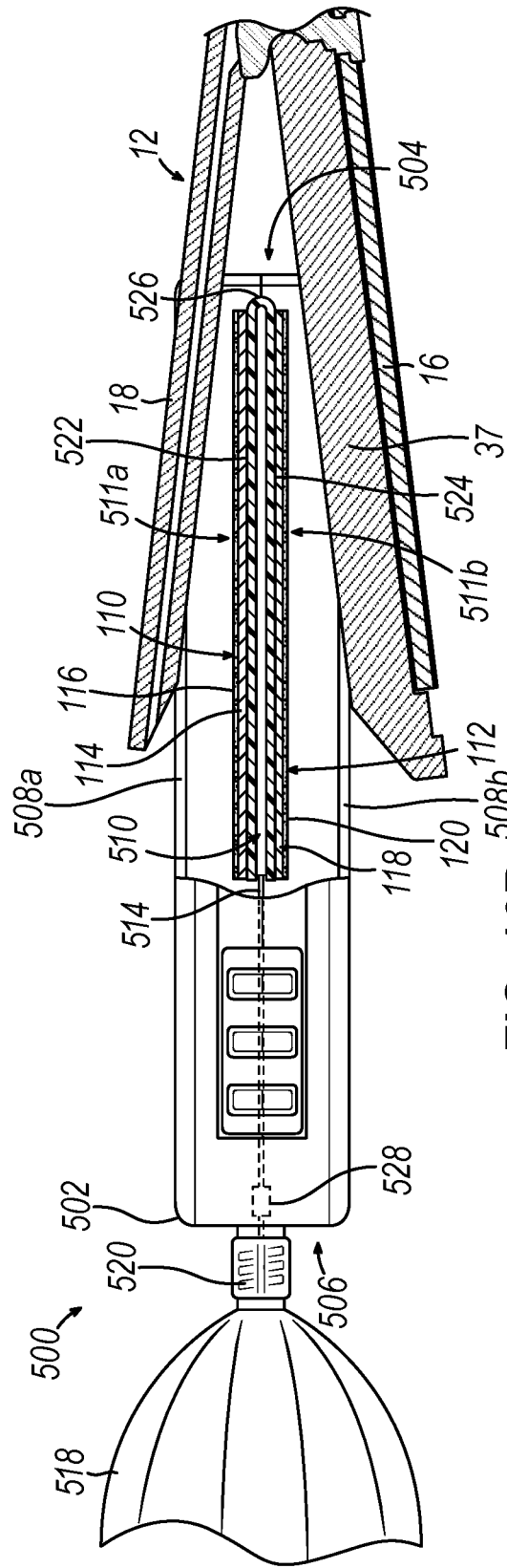

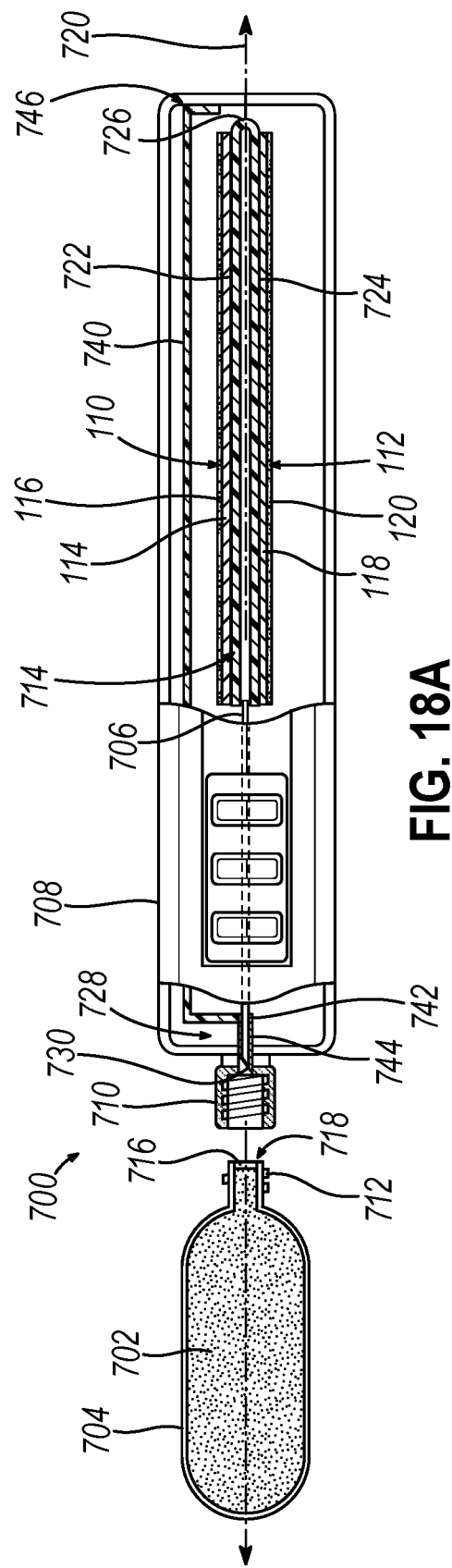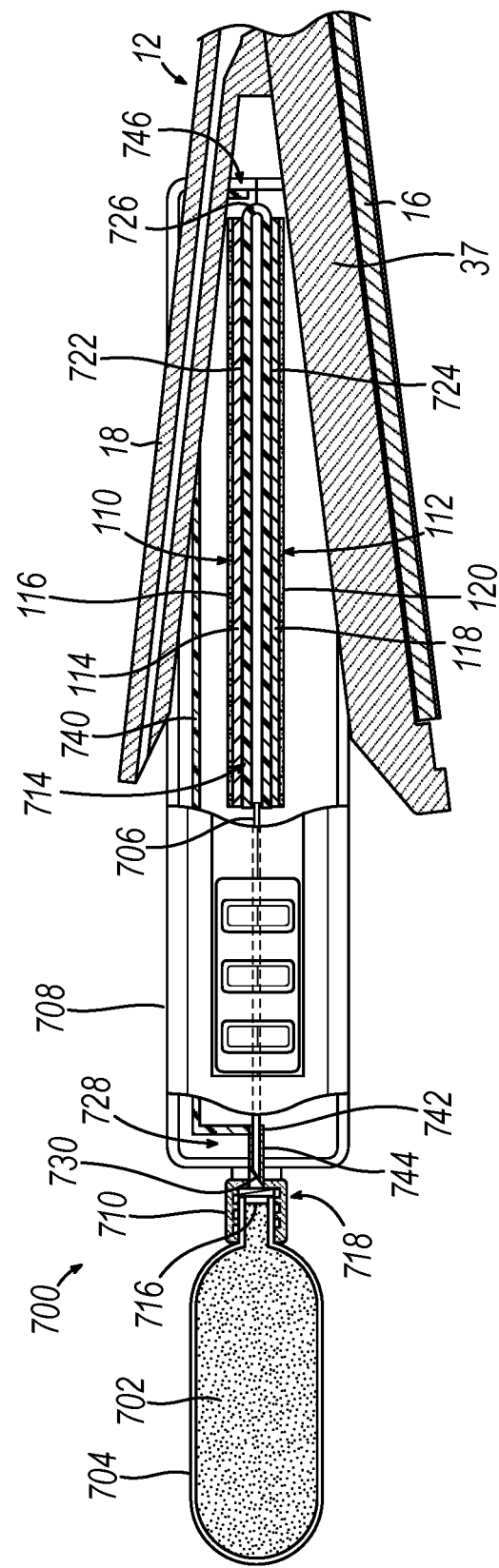

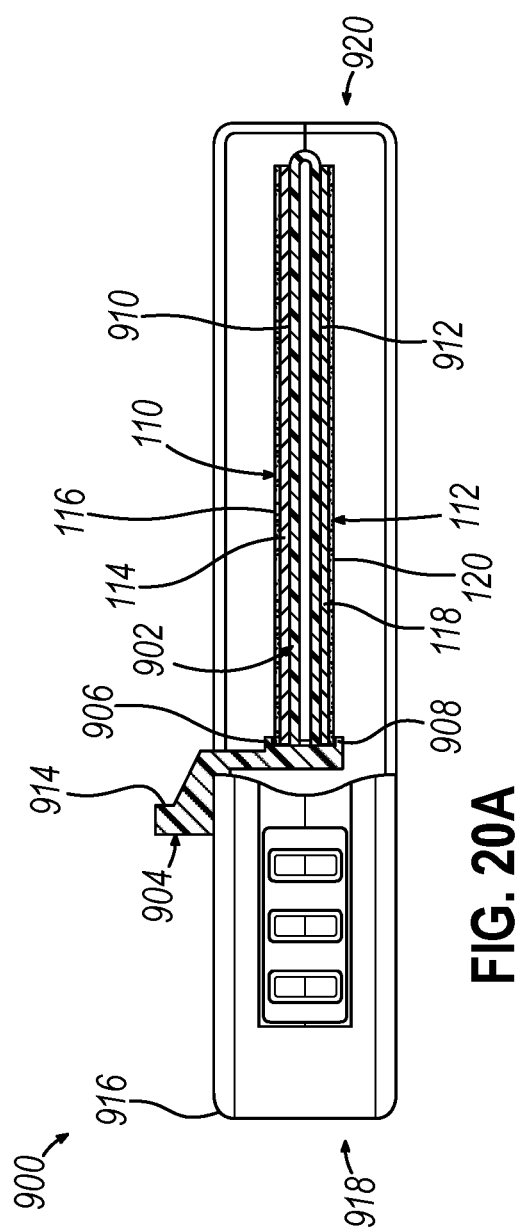

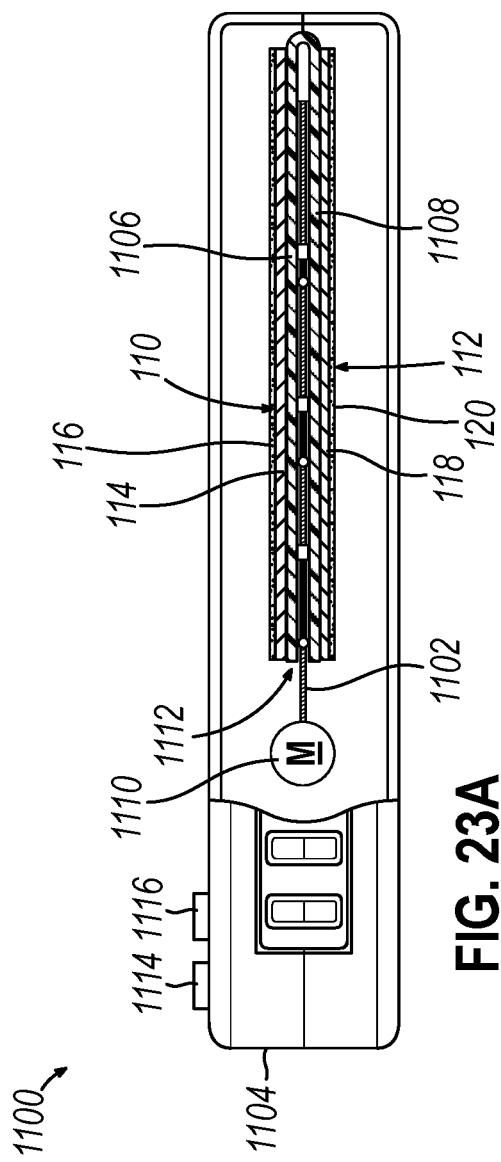
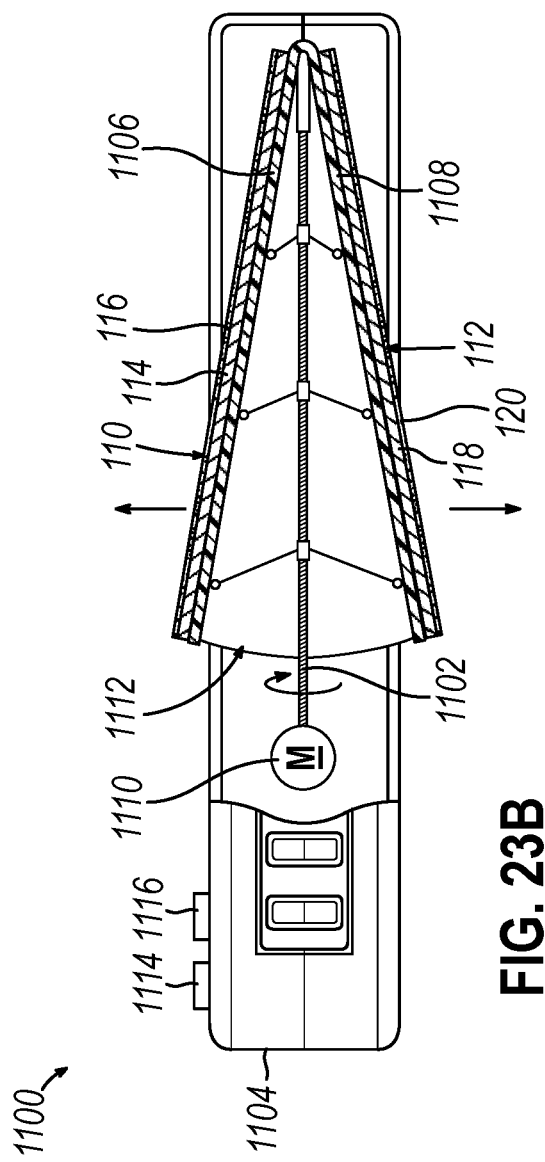
FIG. 23A
FIG. 23B

APPARATUS AND METHOD TO APPLY BUTTRESS TO END EFFECTOR OF SURGICAL STAPLER VIA DRIVEN MEMBER

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 3:
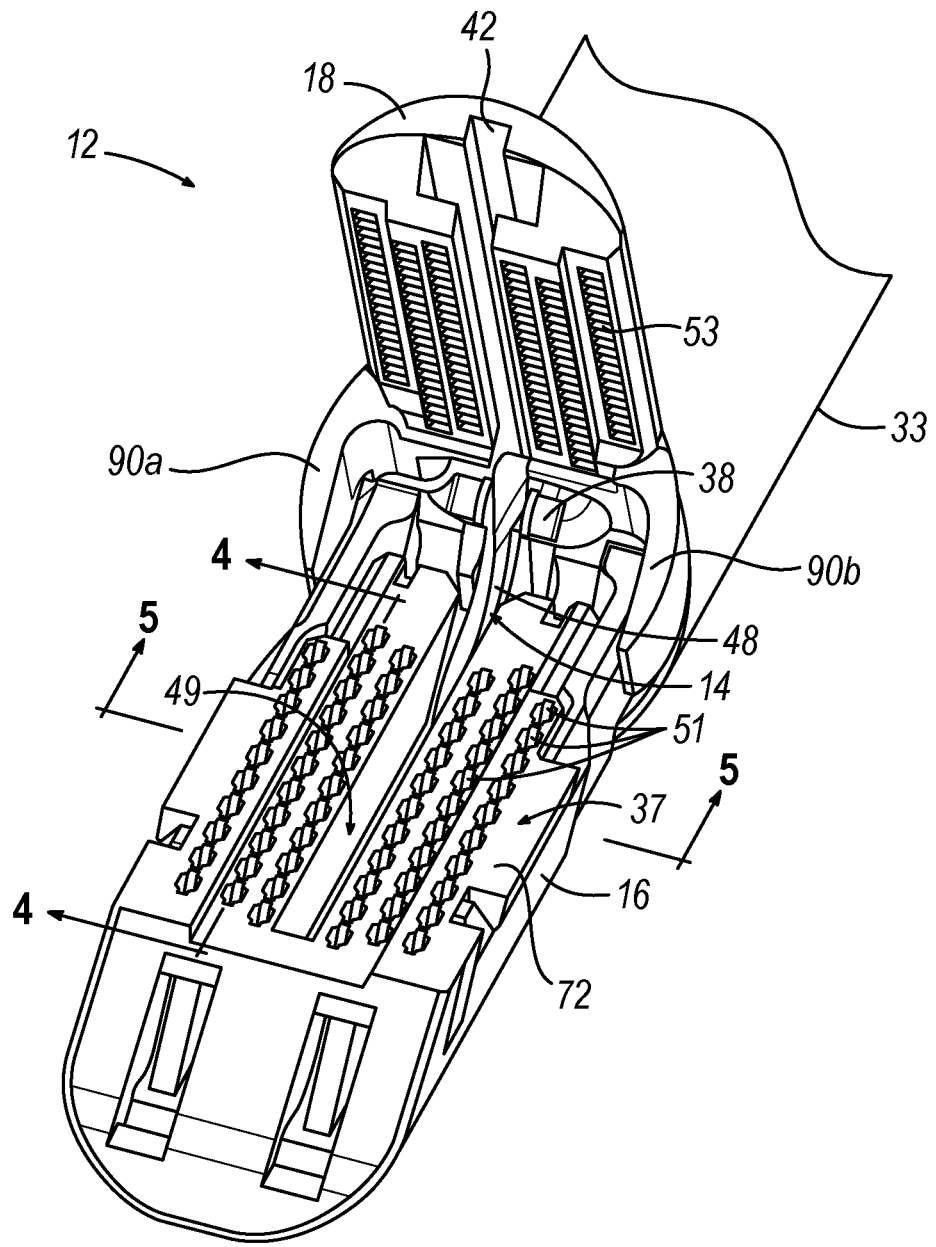
FIG. 3 depicts a perspective view of an end effector of the instrument of FIG. 1 in an open state.
Figure 8:
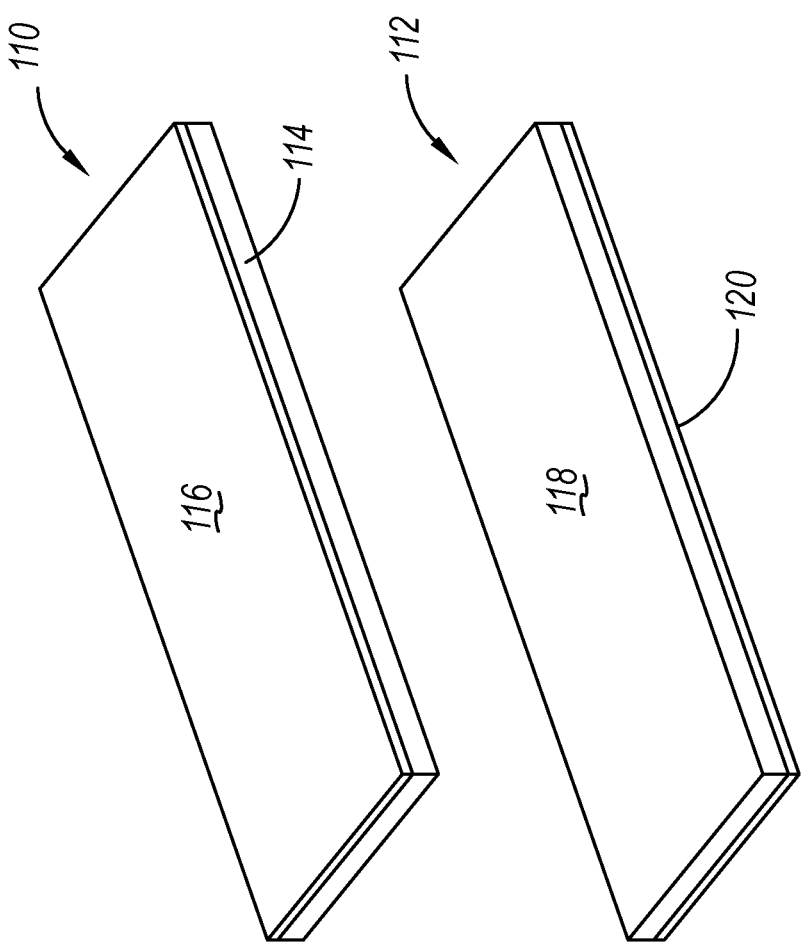
FIG. 8 depicts a perspective view of an exemplary pair of buttress assemblies, each of which may be applied to a jaw of the end effector of FIG. 3.
Figure 16C:
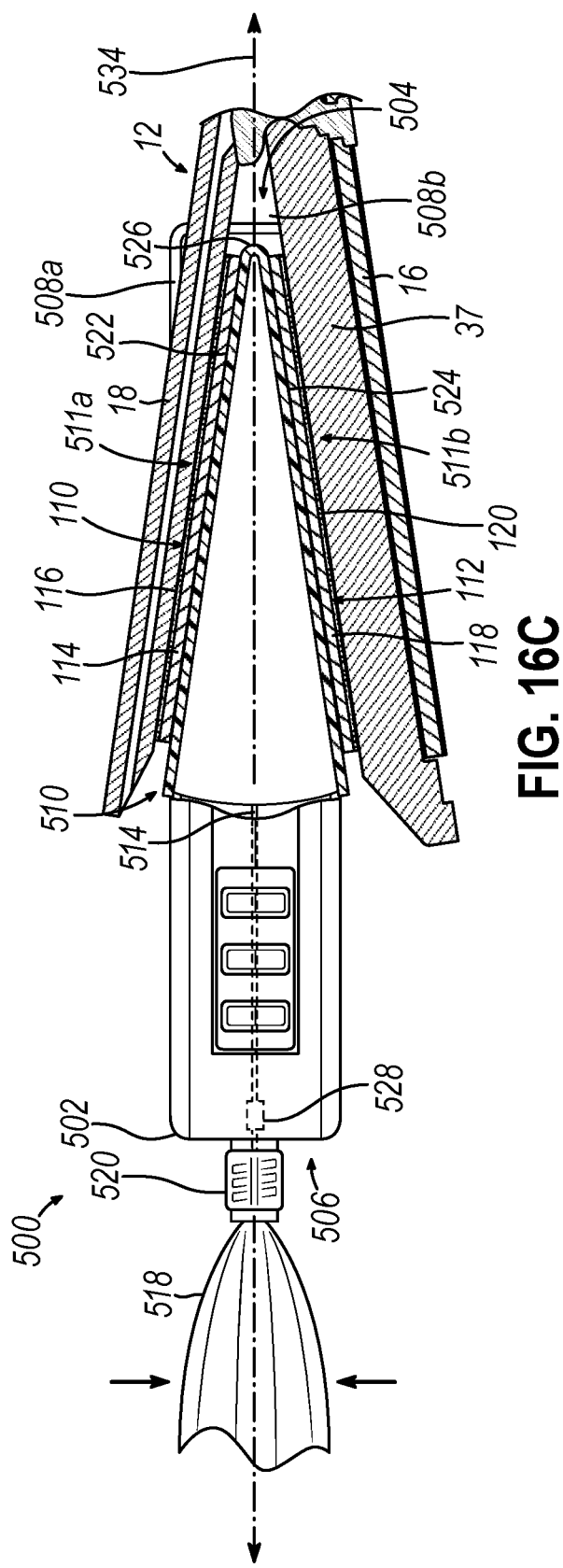
Figure 17:
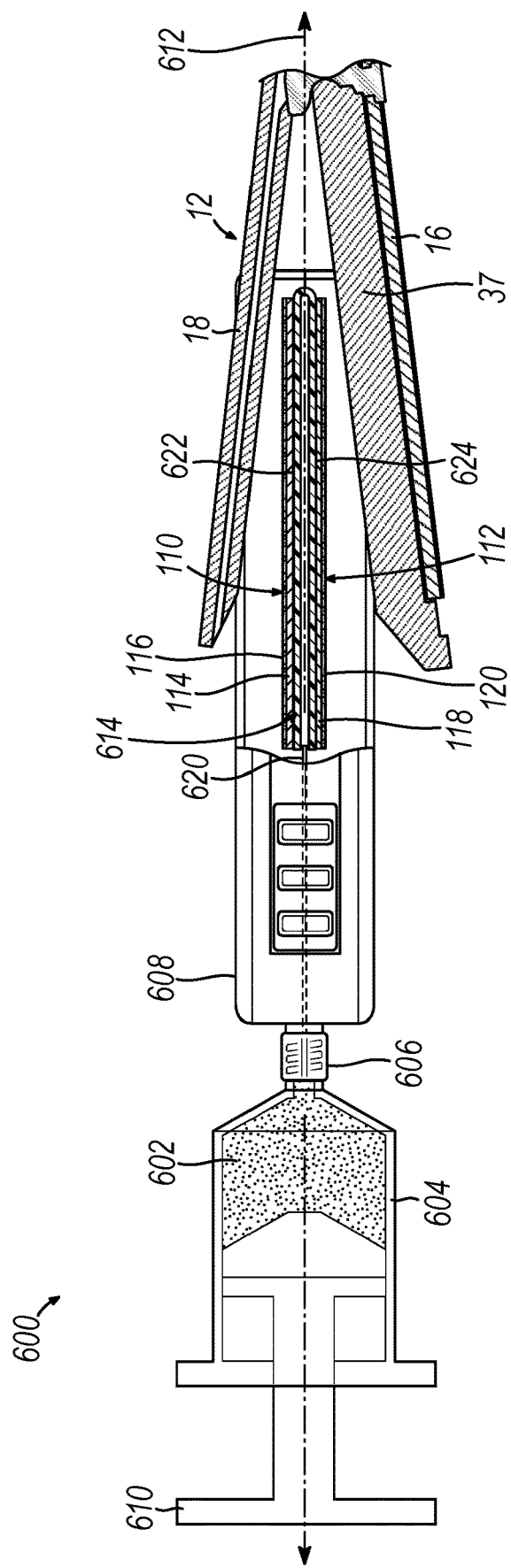
Figure 18C:
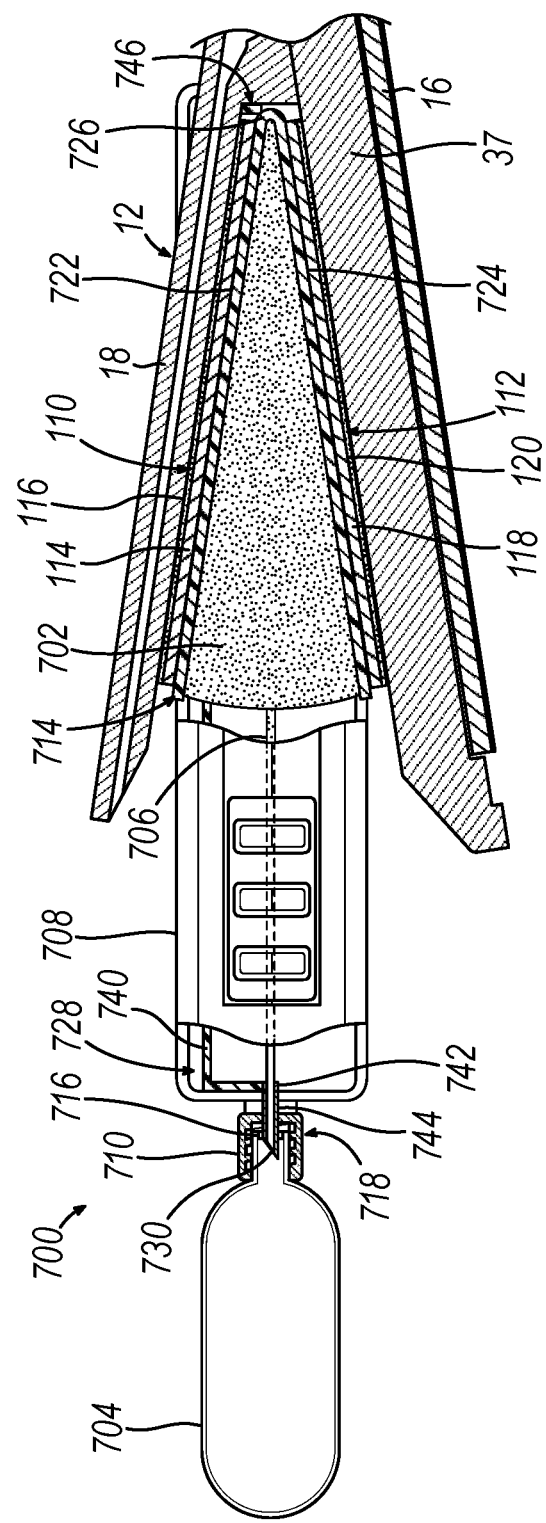
Figure 19A:
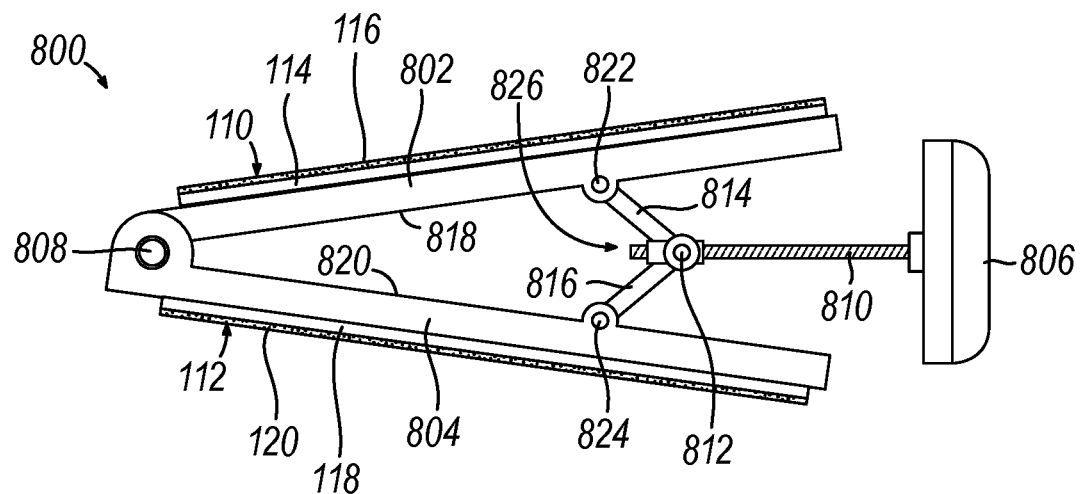
Figure 19B:
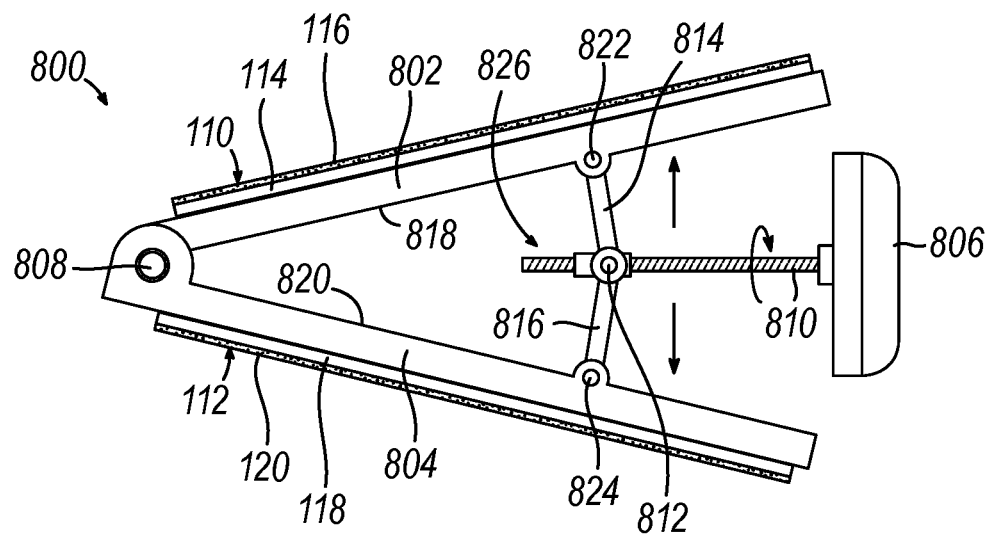
Figure 20C:
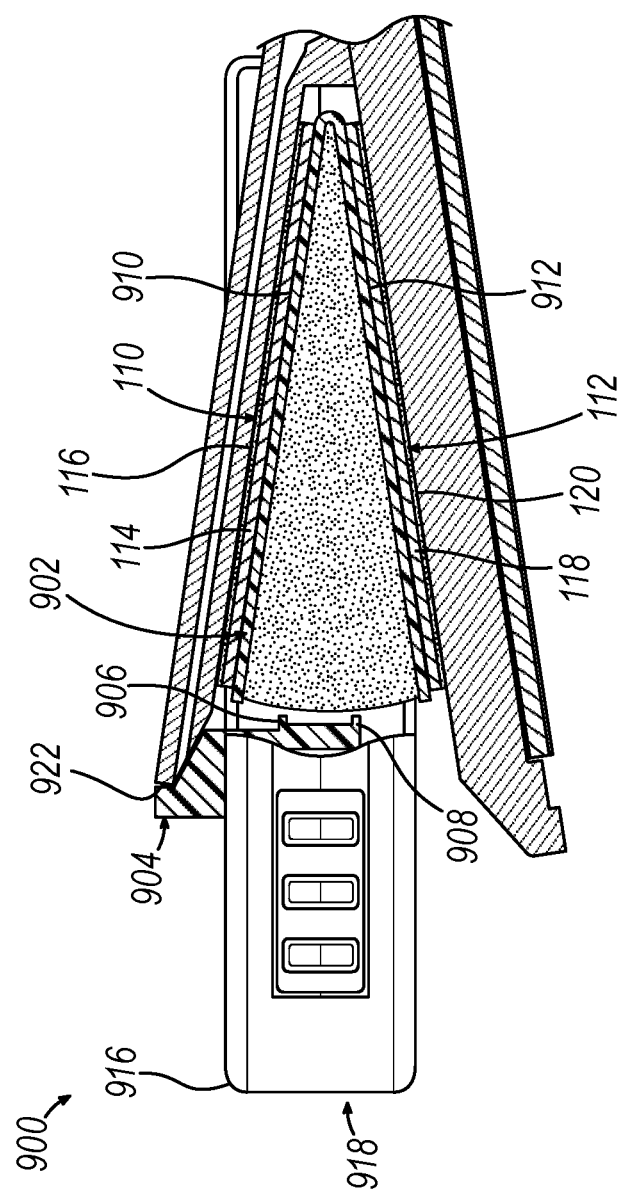
Figure 21A:
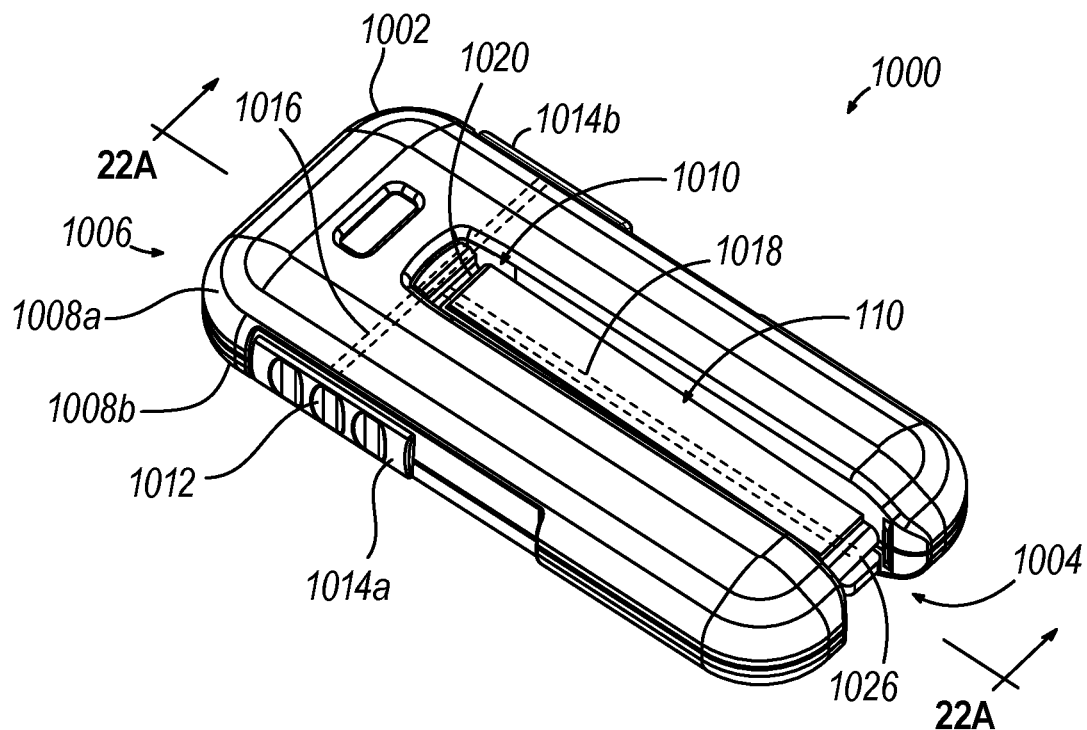
Figure 21B:
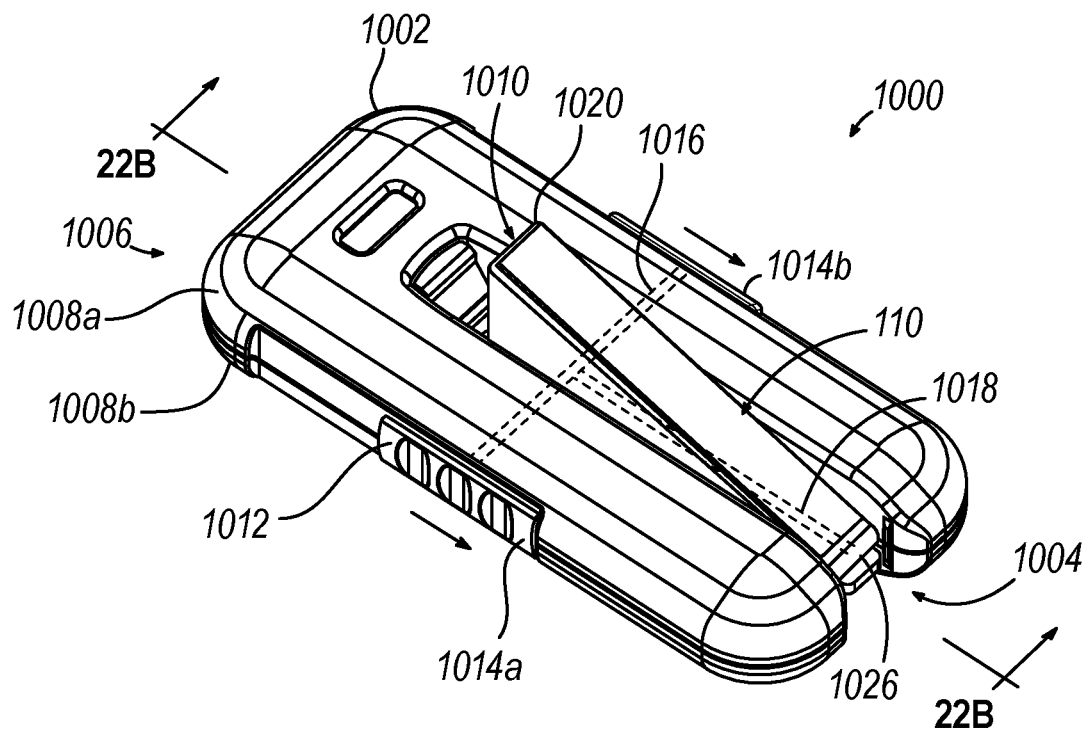
Figure 22A:
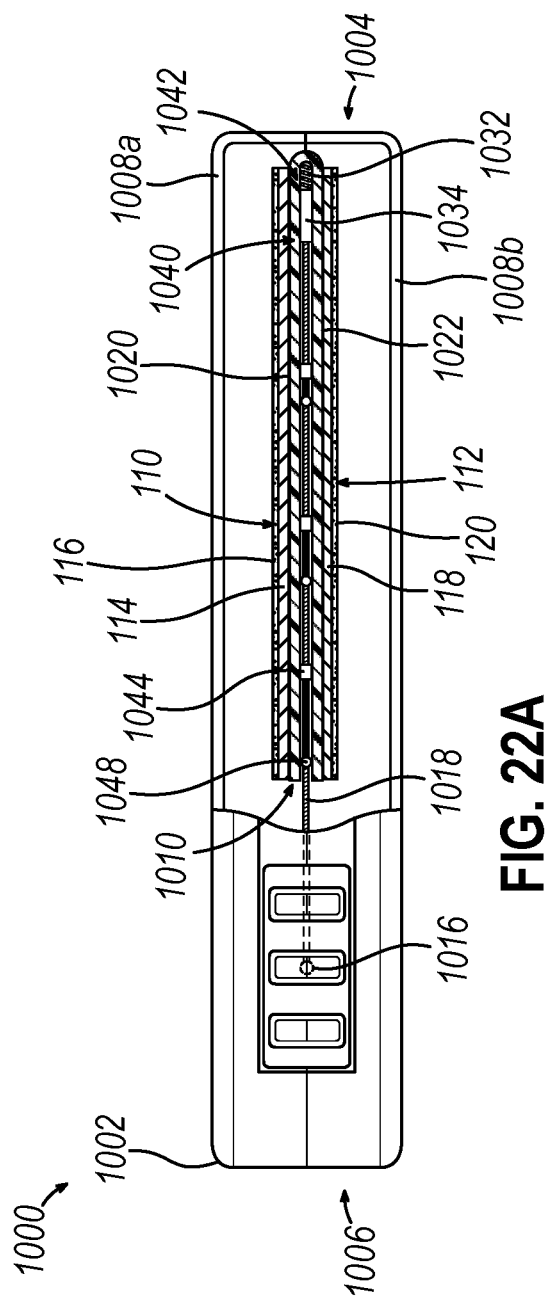
Figure 22B:
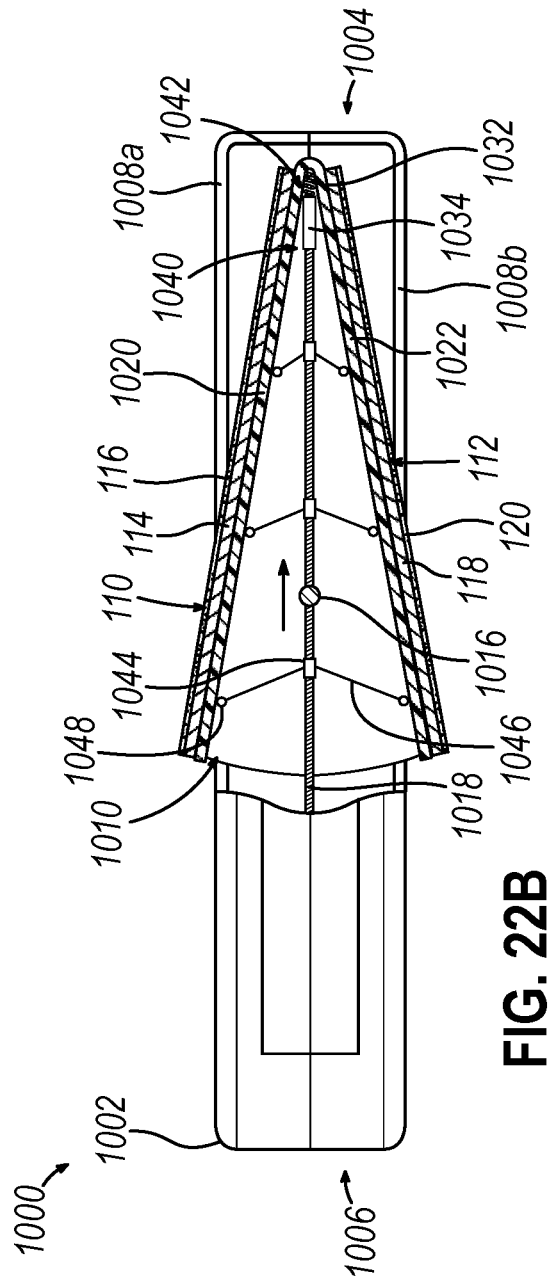
Figure 24A:
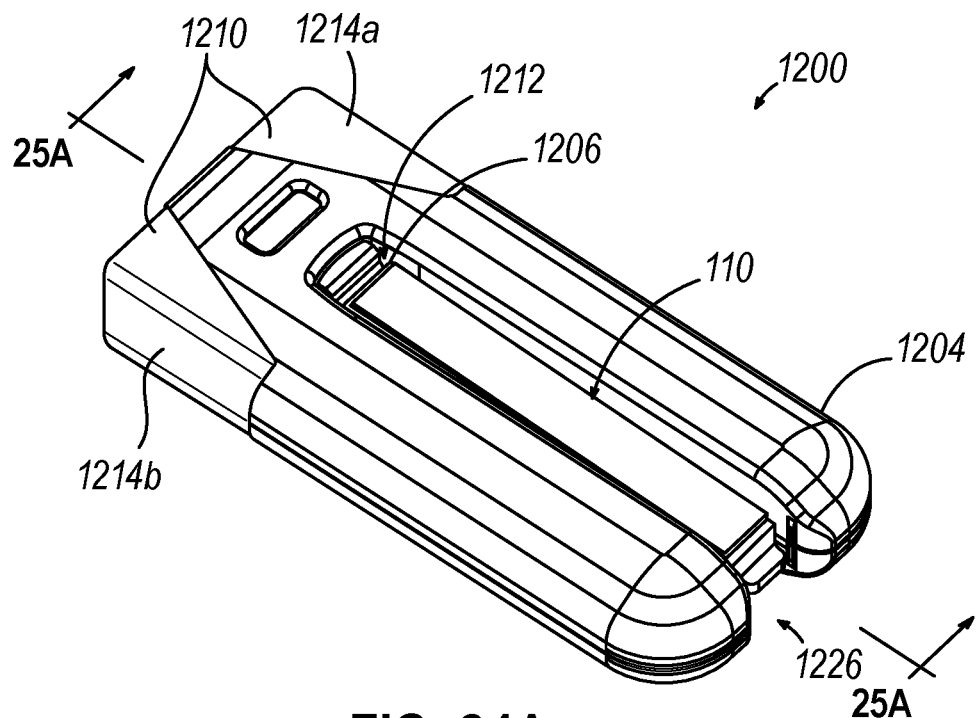
Figure 24B:
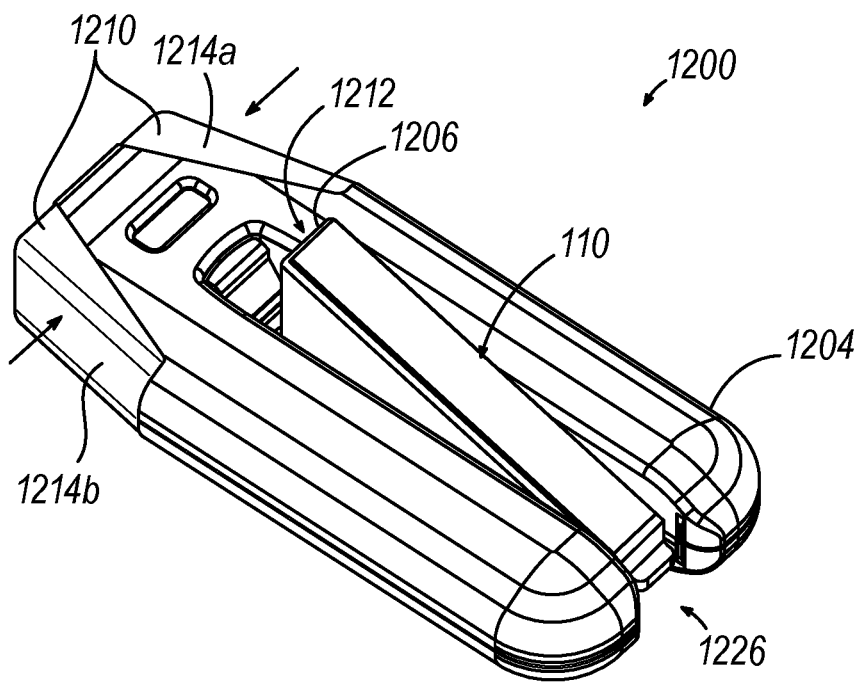
Figure 25A:
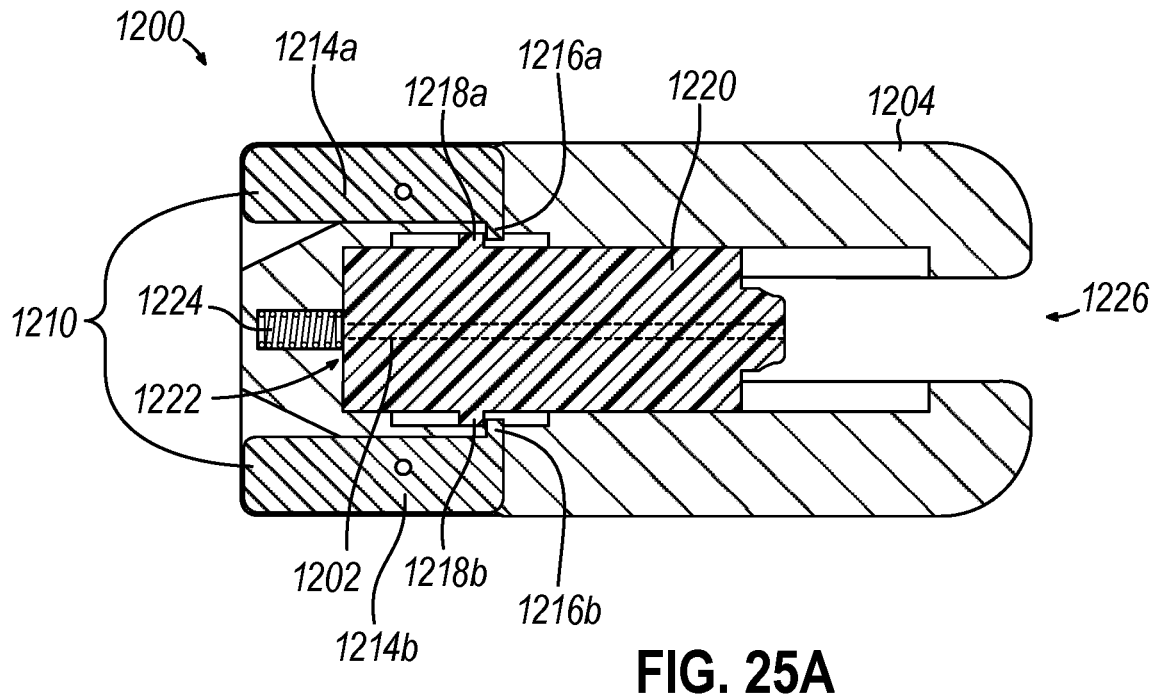
Figure 25B:
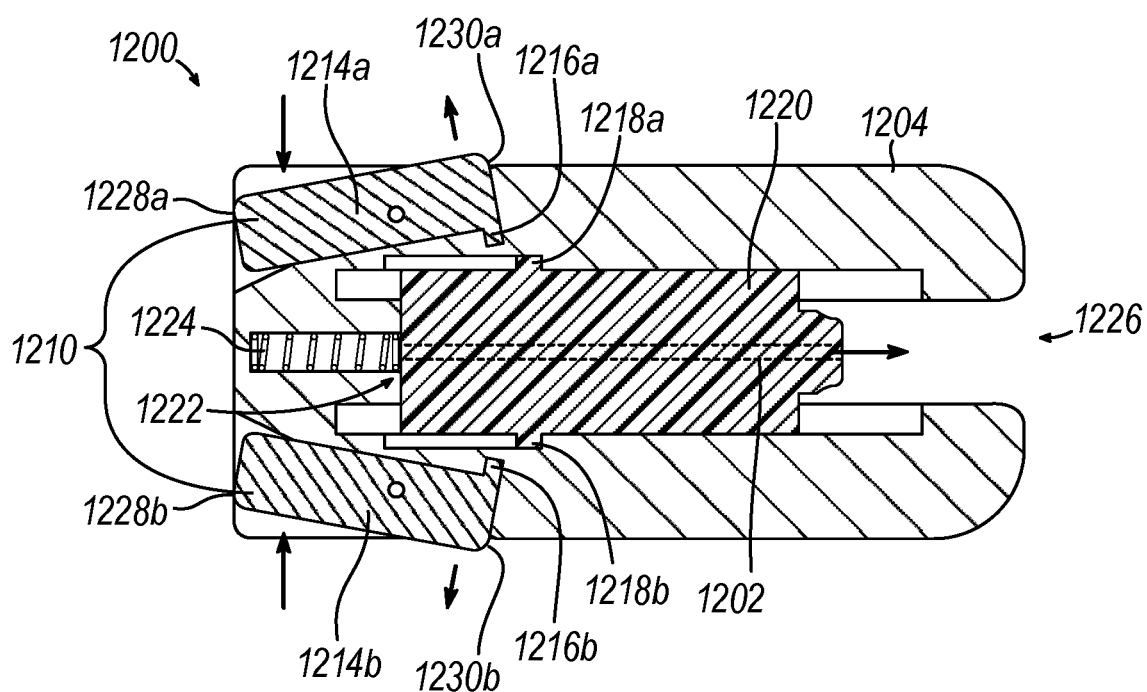
Figure 26A:
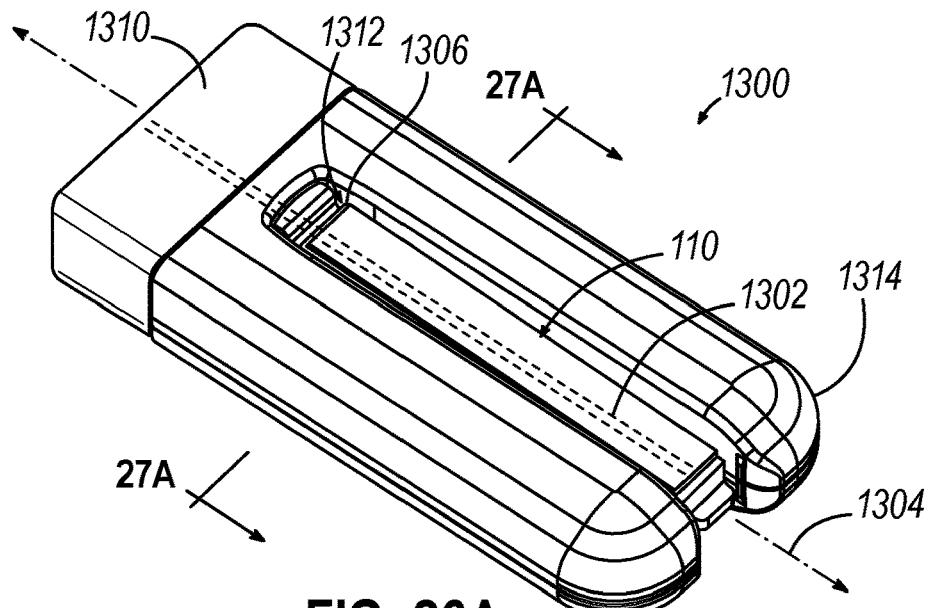
Figure 26B:
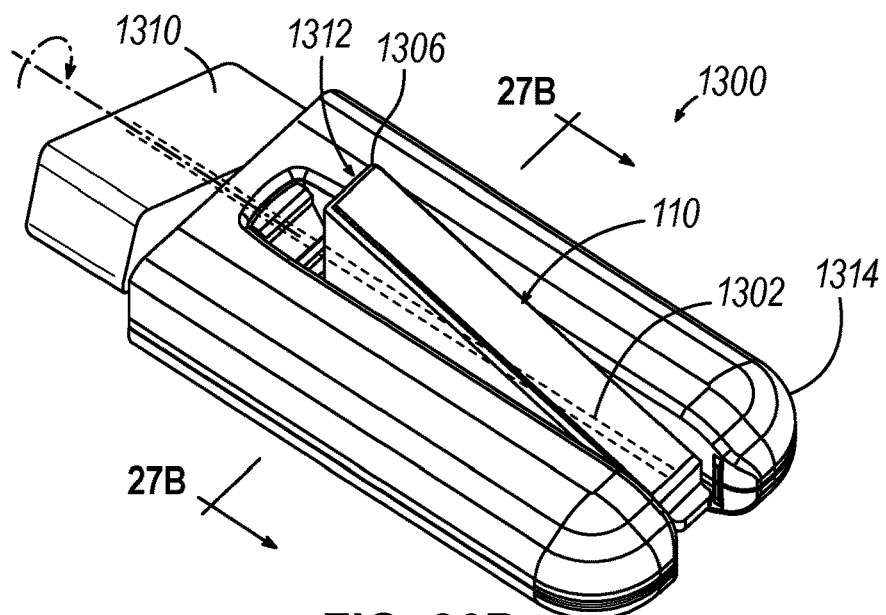
Figure 27A:
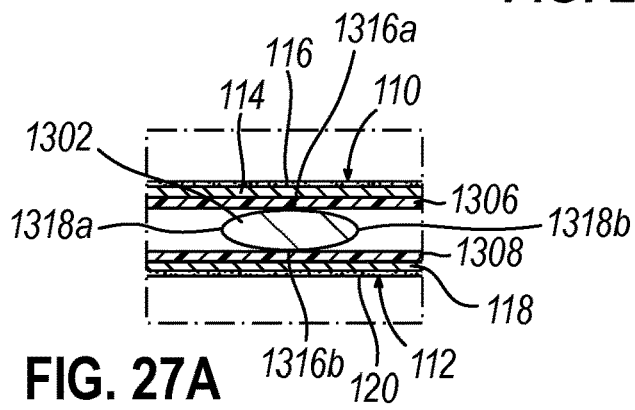
Figure 27B:
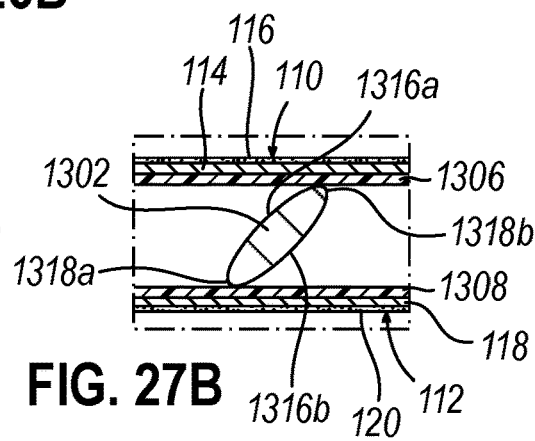
Figure 28A:
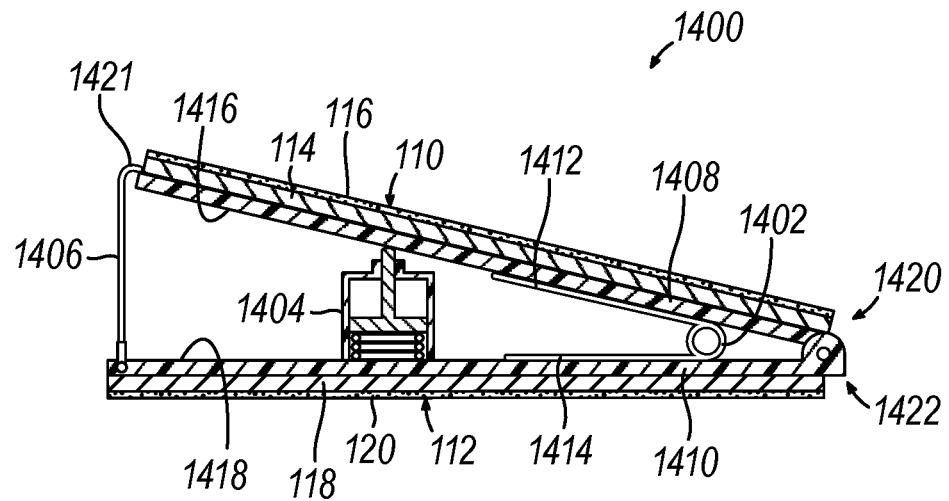
Figure 28B:
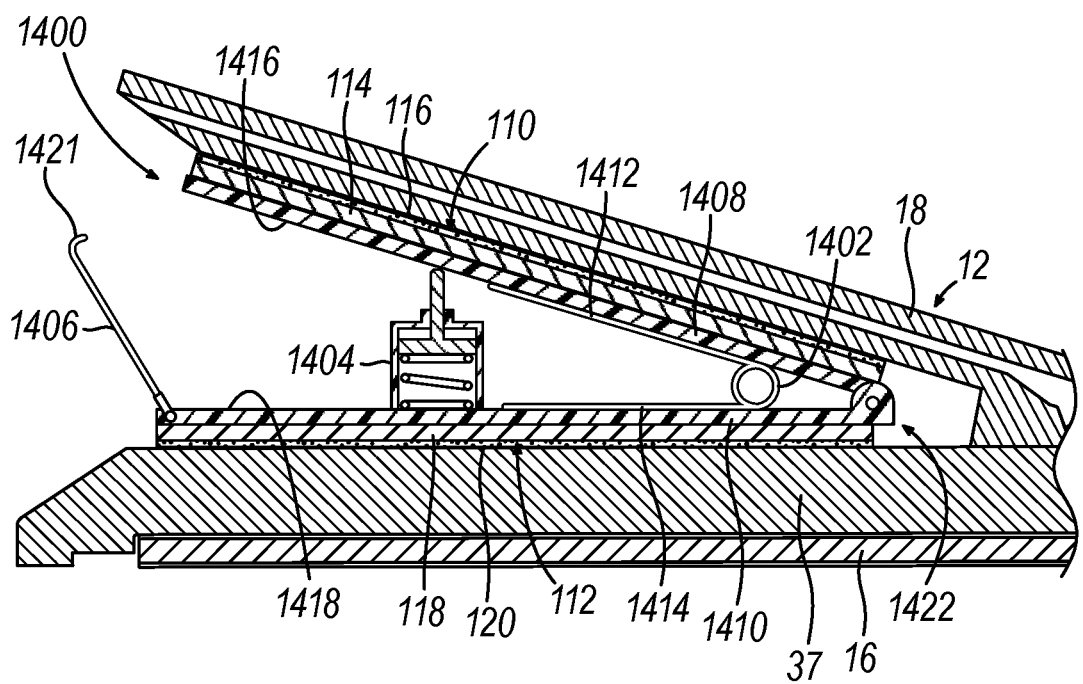

8, and the end effector of FIG. 3, with the applicator device in an expanded state for securing the buttress assembly to the end effector;

FIG. 16A depicts a partial side cross-sectional view of a third exemplary alternative applicator device with the buttress assembly of FIG. 8 applied to the applicator device, showing the applicator device in a non-expanded state;

FIG. 16B depicts a side partial cross-sectional view of the applicator device of FIG. 16A, the buttress assembly of FIG. 8, and the end effector of FIG. 3, with an air pump coupled with the applicator device and in a first state;

FIG. 16C depicts a partial side cross-sectional view of the applicator device of FIG. 16A, the buttress assembly of FIG. 8, and the end effector of FIG. 3, with the air pump coupled with the applicator device and in a second state thereby expanding the applicator device for securing the buttress assembly to the end effector;

FIG. 17 depicts a partial side cross-sectional view of a fourth exemplary alternative applicator device, with the buttress assembly of FIG. 8 applied to the applicator device and with the end effector of FIG. 3 being positioned for application of the buttress assembly, with a fluid injector coupled with the applicator device, showing the applicator device in a non-expanded state;

FIG. 18A depicts a partial side cross-sectional view of a fifth exemplary alternative applicator device with the buttress assembly of FIG. 8 applied to the applicator device, showing the applicator device in a non-expanded state;

FIG. 18B depicts a partial side cross-sectional view of the applicator device of FIG. 18A, the buttress assembly of FIG. 8, and the end effector of FIG. 3, with a compressed air injector coupled with the applicator device and the compressed air being in a first state with the applicator device in the non-expanded state;

FIG. 18C depicts a partial side cross-sectional view of the applicator device of FIG. 18A, the buttress assembly of FIG. 8, and the end effector of FIG. 3, with the compressed air injector coupled with the applicator device and the compressed air being in a second state thereby expanding the applicator device for securing the buttress assembly to the end effector;

FIG. 19A depicts a side elevational view of a sixth exemplary alternative applicator device, with the buttress assembly of FIG. 8 applied to the applicator device and the applicator device in a first, non-expanded state;

FIG. 19B depicts a side elevational view of the applicator device of FIG. 19A, with the applicator device in a second, expanded state to thereby secure the buttress assembly to an end effector;

FIG. 20A depicts a partial side cross-sectional view of a seventh exemplary alternative applicator device with the buttress assembly of FIG. 8 applied to an applicator pad of the applicator device, with the applicator device in a first, non-expanded state;

FIG. 20B depicts a partial side cross-sectional view of the applicator device of FIG. 20A, the buttress assembly of FIG. 8, and the end effector of FIG. 3, with the applicator pad in the first, non-expanded state;

FIG. 20C depicts a partial side cross-sectional view of the applicator device of FIG. 20A, the buttress assembly of FIG. 8, and the end effector of FIG. 3, with the applicator pad being in a second, expanded state to thereby secure the buttress assembly to the end effector;

FIG. 21A depicts a perspective view of an eighth exemplary alternative applicator device, the applicator device being in a first, non-expanded state;

FIG. 21B depicts a perspective view of the applicator device of FIG. 21A, the applicator device being in a second, expanded state;

FIG. 22A depicts a partial side cross-sectional view of the applicator device of FIG. 21A taken along line 22A-22A of FIG. 21A, with the buttress assembly of FIG. 8 applied to the applicator device, the applicator device being in the first, non-expanded state;

FIG. 22B depicts a partial side cross-sectional view of the applicator device of FIG. 21A taken along line 22B-22B of FIG. 21B, with the buttress assembly of FIG. 8 applied to the applicator device, the applicator device being in the second, expanded state to thereby secure the buttress assembly to an end effector;

FIG. 23A depicts a partial side cross-sectional view of a ninth exemplary alternative applicator device, with the buttress assembly of FIG. 8 applied to the applicator device, the applicator device being in a first, non-expanded state;

FIG. 23B depicts a partial side cross-sectional view of the applicator device of FIG. 23A, with the buttress assembly of FIG. 8 applied to the applicator device, the applicator device being in a second, expanded state to thereby secure the buttress assembly to an end effector;

FIG. 24A depicts a perspective view of a tenth exemplary alternative applicator device, the applicator device being in a first, non-expanded state;

FIG. 24B depicts a perspective view of the applicator device of FIG. 24A, the applicator device being in a second, expanded state to thereby secure the buttress assembly to an end effector;

FIG. 25A depicts a top cross-sectional view of the applicator device of FIG. 24A taken along line 25A-25A of FIG. 24A, the applicator device being in the first, non-expanded state;

FIG. 25B depicts a top cross-sectional view of the applicator device of FIG. 24A taken along line 25A-25A of FIG. 24A, the applicator device being in the second, expanded state to thereby secure the buttress assembly to an end effector;

FIG. 26A depicts a perspective view of an eleventh exemplary alternative applicator device, the applicator device being in a first, non-expanded state;

FIG. 26B depicts a perspective view of the applicator device of FIG. 26A, the applicator device being in a second, expanded state to thereby secure the buttress assembly to an end effector;

FIG. 27A depicts a partial cross-sectional view of the applicator device of FIG. 26A taken along line 27A-27A of FIG. 26A, the applicator device being in the first, non-expanded state;

FIG. 27B depicts a partial cross-sectional view of the applicator device of FIG. 26A taken along line 27B-27B of FIG. 26B, the applicator device being in the second state, expanded to thereby secure the buttress assembly to an end effector;

FIG. 28A depicts a side cross-sectional view of a twelfth exemplary alternative applicator device, with the buttress assembly of FIG. 8 applied to the applicator device, the applicator device being in a first, non-expanded state; and FIG. 28B depicts a side cross-sectional view of the applicator device of FIG. 28A and the end effector of FIG. 3, with the buttress assembly of FIG. 8 applied to the applicator device, the applicator device being in a second, expanded state to thereby secure the buttress assembly to the end effector.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. EXEMPLARY SURGICAL STAPLER

FIGS. 1-7 depict an exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) of the present example includes a lower jaw (16) that includes a staple cartridge (37), and an upper jaw in the form of a pivotable anvil (18).

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 1:
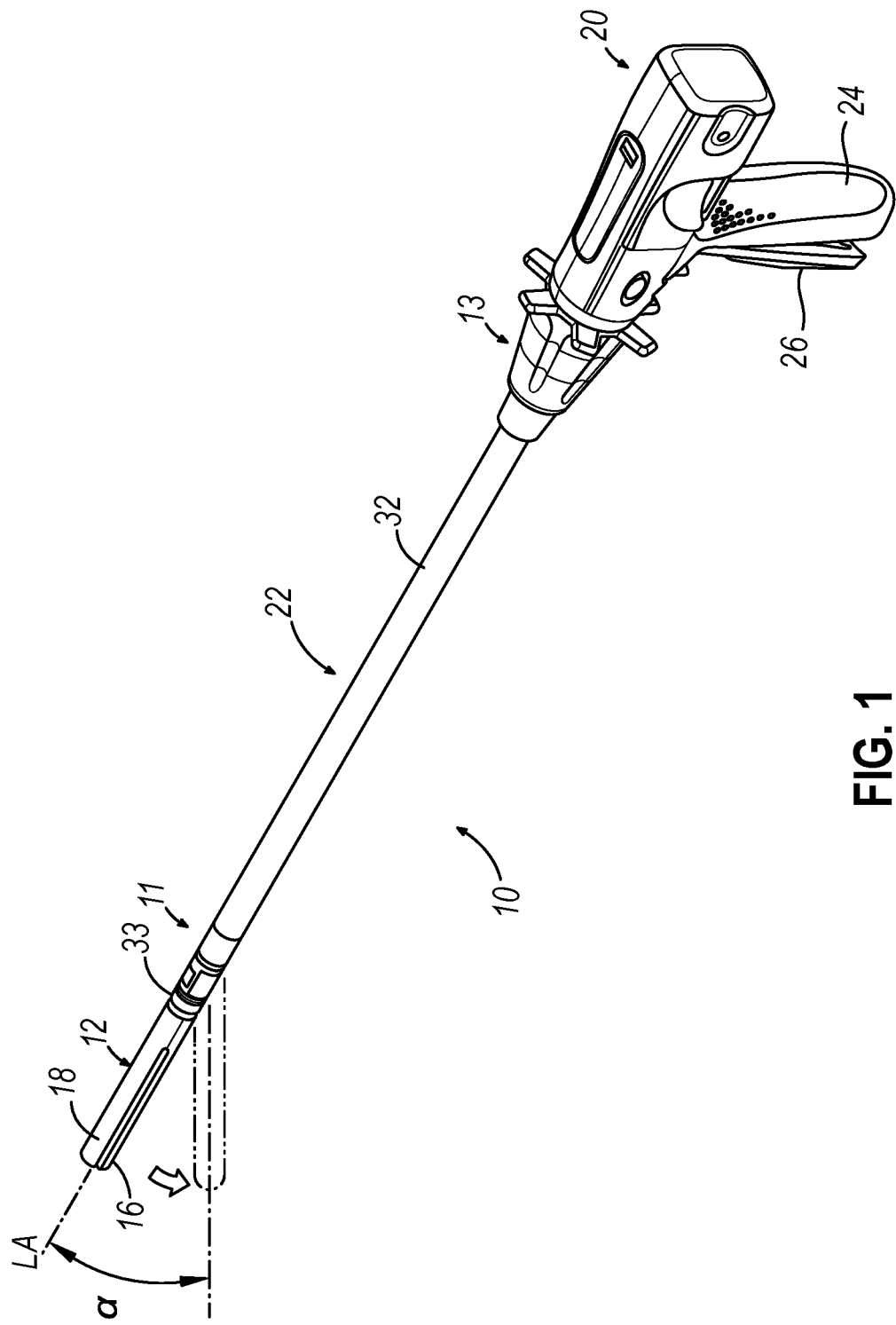
FIG. 1 depicts a perspective view of an exemplary surgical stapling instrument.
Figure 2:
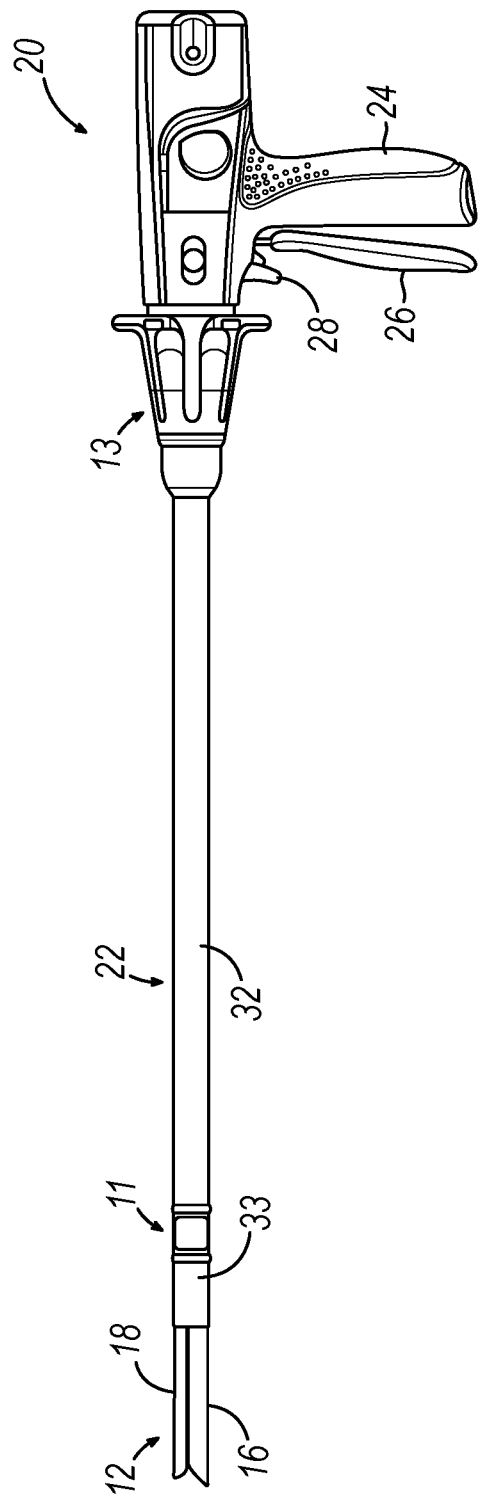
FIG. 2 depicts a side elevational view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 4A:
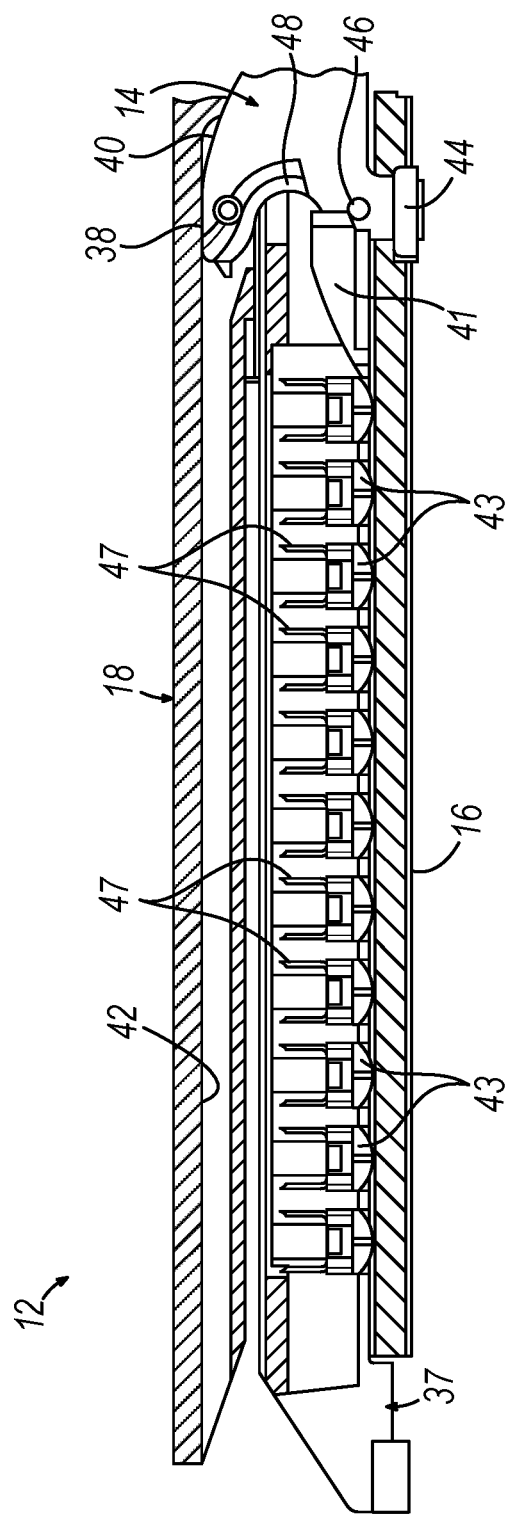
FIG. 4A depicts a side cross-sectional view of the end effector of FIG. 3, taken along line 4-4 of FIG. 3, with a firing beam in a proximal position.
Figure 4B:
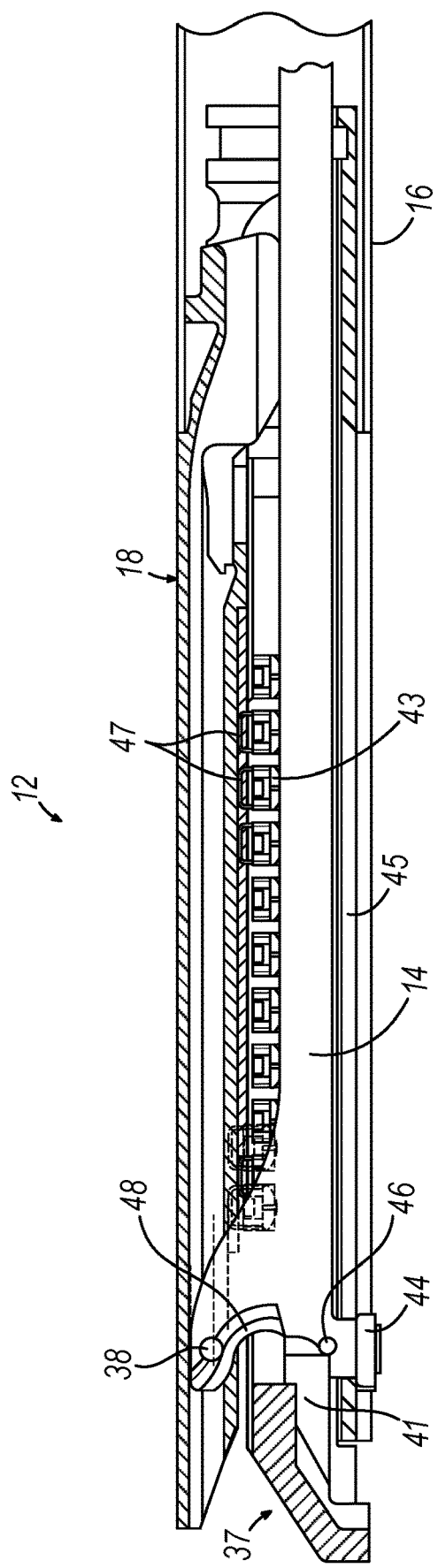
FIG. 4B depicts a side cross-sectional view of the end effector of FIG. 3, taken along line 4-4 of FIG. 3, with the firing beam in a distal position.
Figure 5:
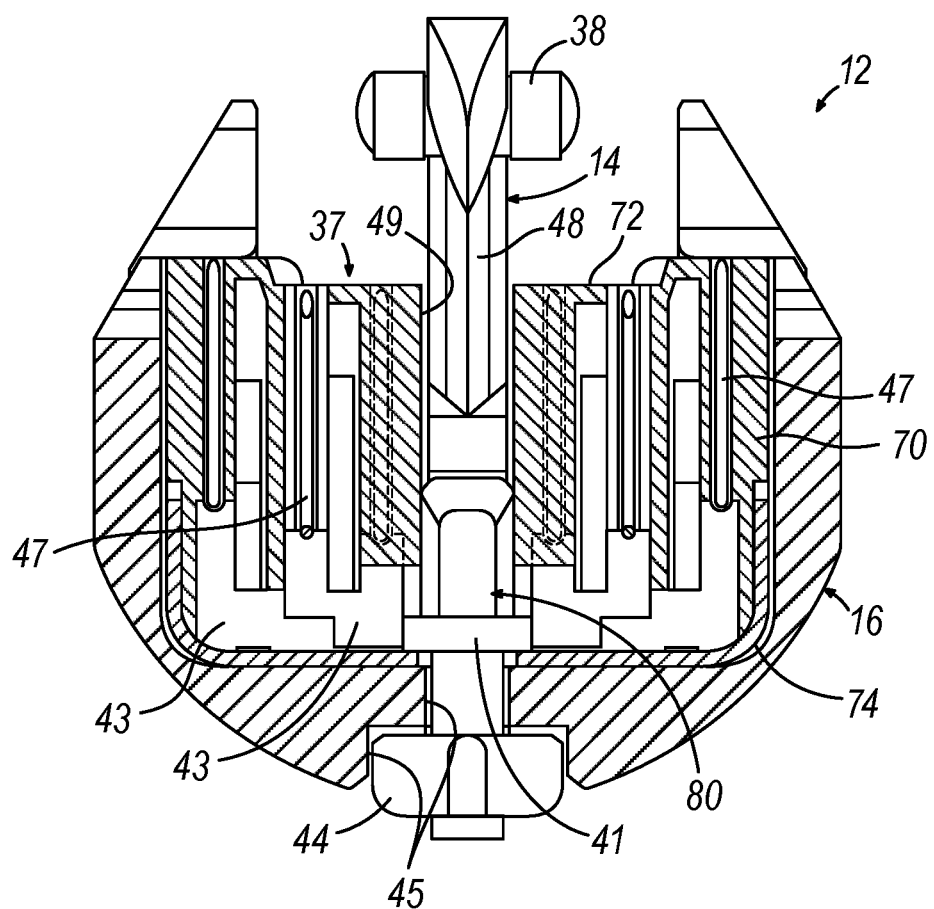
FIG. 5 depicts an end cross-sectional view of the end effector of FIG. 3, taken along line 5-5 of FIG. 3.
Figure 6:
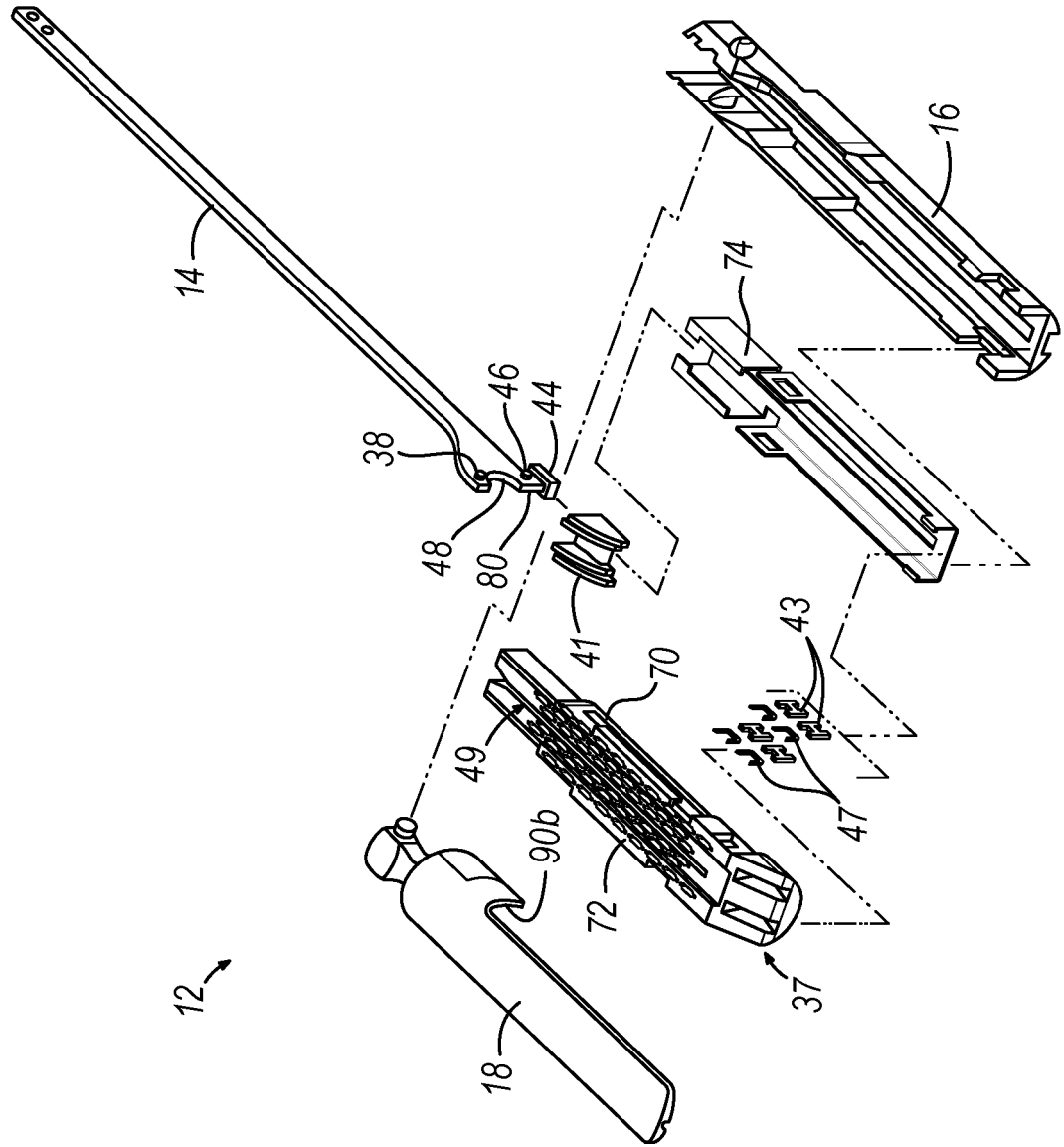
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), firing beam (14) is then advanced distally into engagement with anvil (18) by having upper pin (38) enter longitudinal anvil slot (42). A pusher block (80) (shown in FIG. 5) located at the distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil (18) is intentionally omitted from the view in FIG. 5.

Figure 7:
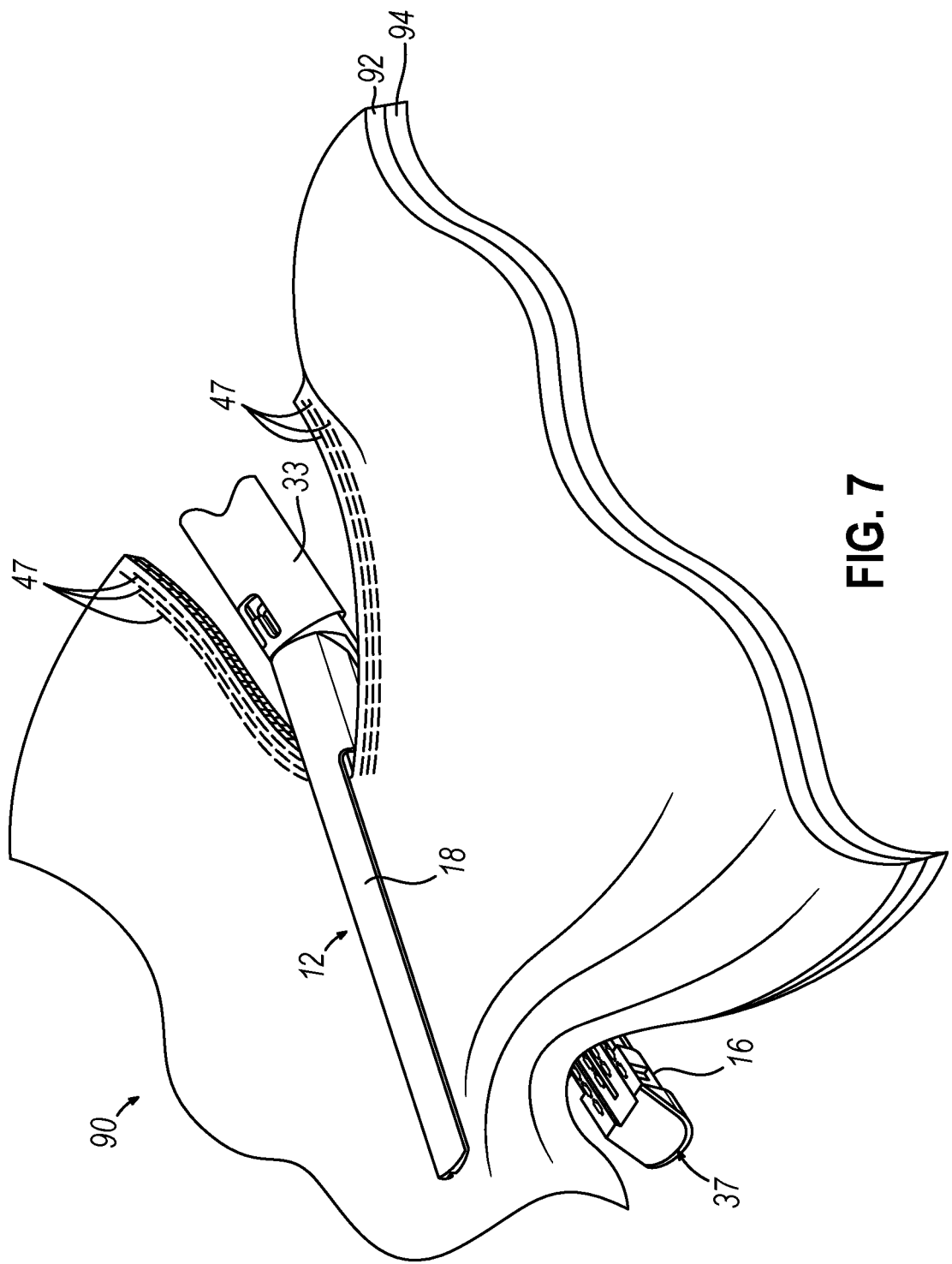
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through the tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. EXEMPLARY BUTTRESS ASSEMBLY AND BUTTRESS APPLIER CARTRIDGE

In some instances, it may be desirable to equip end effector (12) of surgical instrument (10) with an adjunct material, such as a buttress, to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (43). In some other instances, a buttress may be provided on the surface of anvil (18) that faces staple cartridge (37). It should also be understood that a first buttress may be provided on upper deck (72) of staple cartridge (37) while a second buttress is provided on anvil (18) of the same end effector (12).

Various examples of forms that a buttress may take will be described in greater detail below. Various ways in which a buttress may be secured to a staple cartridge (37) or an anvil (18) will also be described in greater detail below. Exemplary buttress assemblies, exemplary materials and techniques for applying buttress assemblies, and exemplary buttress applier cartridges may be configured in accordance with at least some of the teachings of U.S. Pat. No. 10,166,023, entitled "Method of Applying a Buttress to a Surgical Stapler End Effector," issued Jan. 1, 2019; and/or in U.S. Pat. No. 10,349,939, entitled "Method of Applying a Buttress to a Surgical Stapler," issued Jul. 16, 2019, the disclosures of which are incorporated by reference herein.

A. Exemplary Composition of Buttress Assembly

FIG. 8 shows an exemplary pair of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (47). By way of example only, each buttress body (114, 118) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to underside (124) of anvil (18). Similarly, adhesive layer (120) is provided on buttress body (118) to adhere buttress body (118) to upper deck (72) of staple cartridge (37). Such an adhesive material may provide proper positioning of buttress body (114, 118) before and during actuation of end effector (12); then allow buttress body (114, 118) to separate from end effector (12) after end effector (12) has been actuated, without causing damage to buttress body (114, 118) that is substantial enough to compromise the proper subsequent functioning of buttress body (114, 118).

B. Exemplary Stapling of Tissue with Buttress Assemblies

Figure 9:
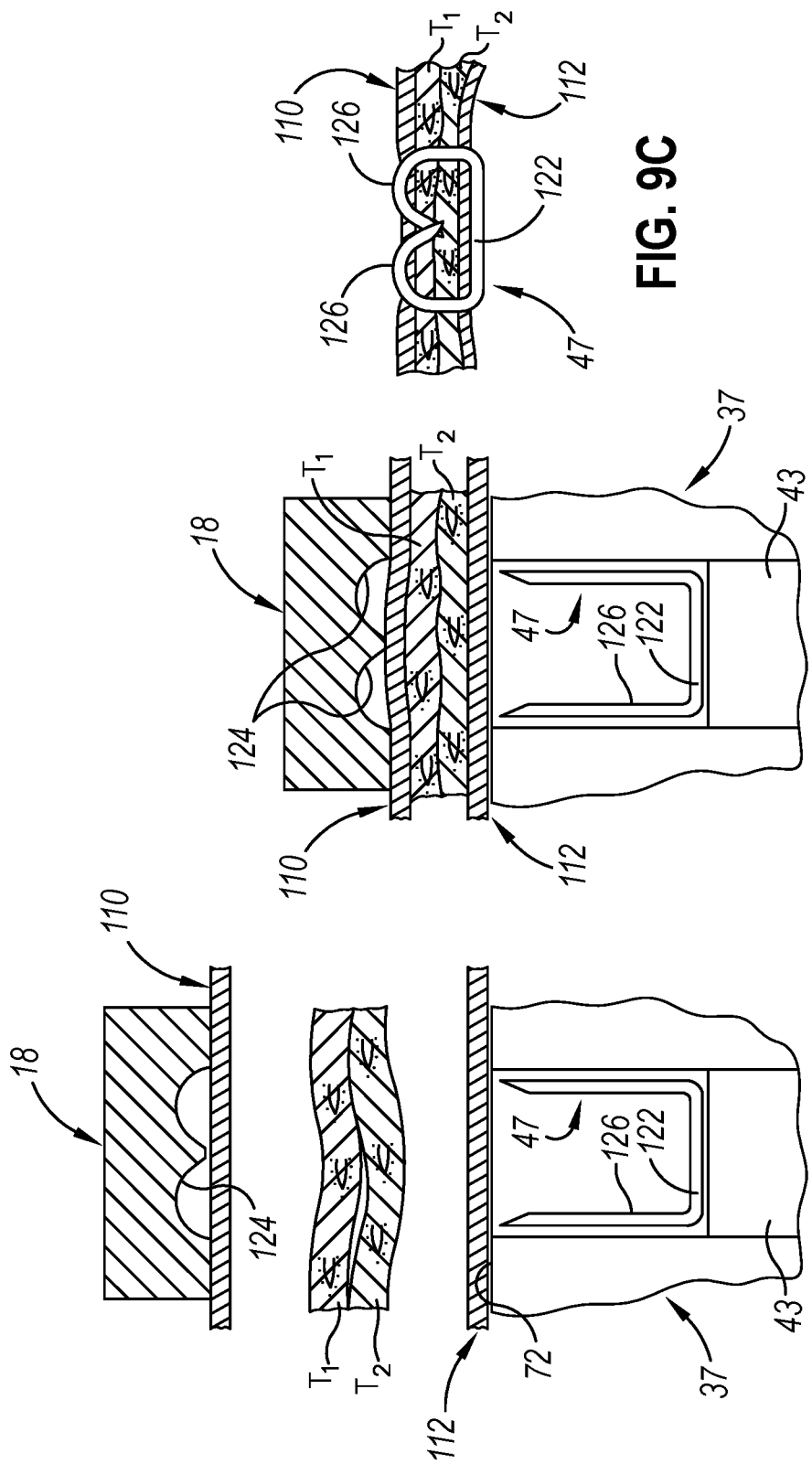
FIG. 9A depicts a cross-sectional end view of a portion of the end effector of FIG. 3 with the buttress assemblies of FIG. 8 applied to the upper and lower jaws of the end effector, showing the end effector jaws in an open state with tissue positioned between the upper and lower jaws.
FIG. 9B depicts a cross-sectional end view of the end effector and buttress assemblies of FIG. 9A, showing the end effector jaws in a closed state on the tissue.
FIG. 9C depicts a cross-sectional view of a formed staple and the buttress assemblies of FIG. 9A after having been secured to the tissue by the end effector of FIG. 3.

FIGS. 9A-9C show an exemplary sequence in which surgical stapler end effector (12), which has been loaded with buttress assemblies (110, 112), is actuated to drive staples (47) through two opposed layers of tissue ($T_1$, $T_2$), with buttress assemblies (110, 112) being secured to the same layers of tissue ($T_1$, $T_2$) by staples (47). In particular, FIG. 9A shows layers of tissue ($T_1$, $T_2$) positioned between anvil (18) and staple cartridge (37), with anvil (18) in the open position. Buttress assembly (110) is adhered to underside (124) of anvil (18) via adhesive layer (116); while buttress assembly (112) is adhered to upper deck (72) of staple cartridge (37) via adhesive layer (120). Layers of tissue ($T_1$, $T_2$) are thus interposed between buttress assemblies (110, 112). Next, closure trigger (26) is pivoted toward pistol grip (24) to drive closure tube (32) and closure ring (33) distally. This drives anvil (18) to the closed position as shown in FIG. 9B. At this stage, layers of tissue ($T_1$, $T_2$) are compressed between anvil (18) and staple cartridge (37), with buttress assemblies (110, 112) engaging opposite surfaces of tissue layers ($T_1$, $T_2$). End effector (12) is then actuated as described above, driving staple (47) through buttress assemblies (110, 112) and tissue ($T_1$, $T_2$). As shown in FIG. 13C, crown (122) of driven staple (47) captures and retains buttress assembly (112) against layer of tissue ($T_2$). Deformed legs (126) of staple (47) capture and retain buttress assembly (110) against layer of tissue ($T_1$).

Figure 10:
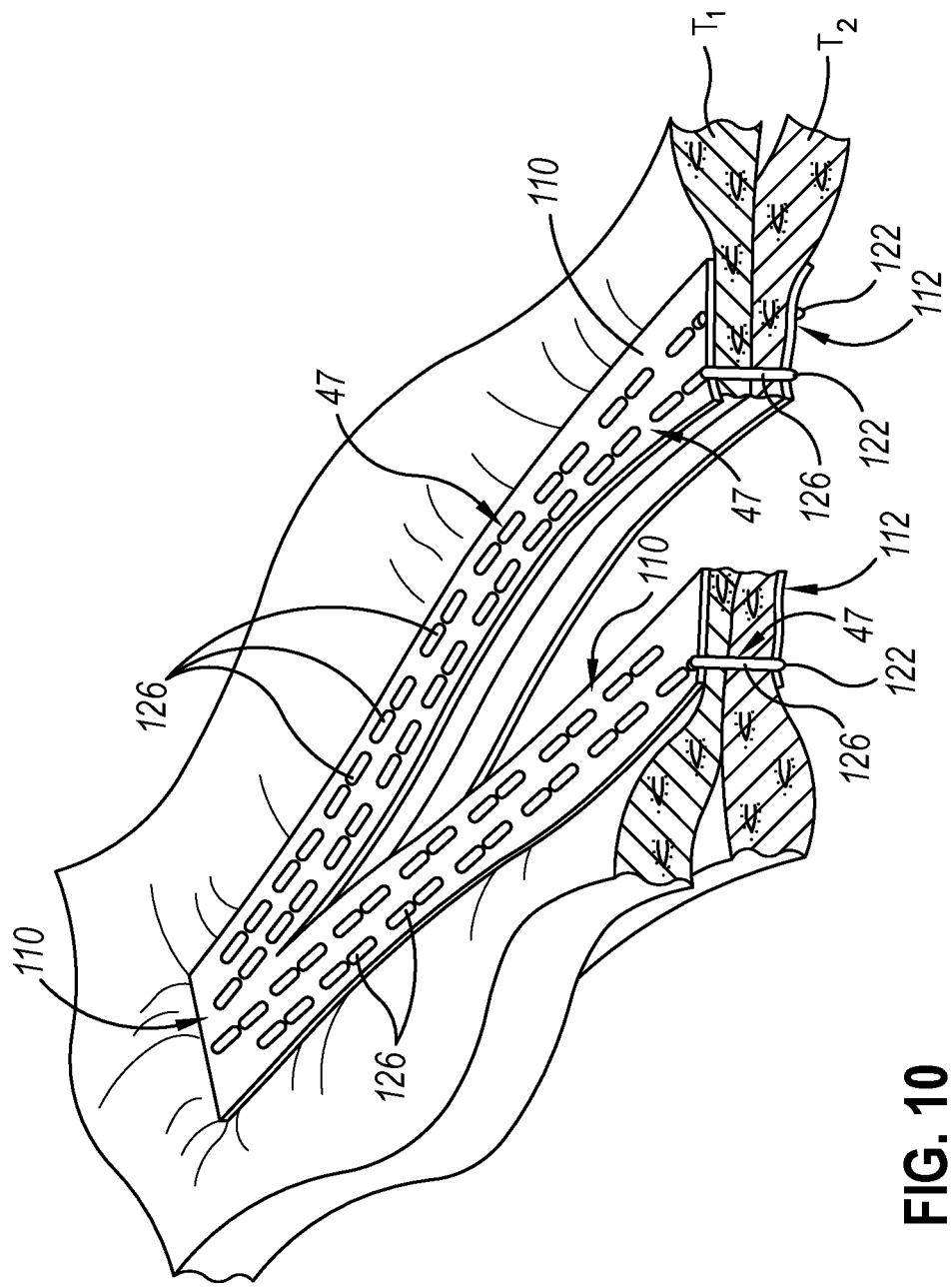
FIG. 10 depicts a perspective view of formed staples and the buttress assemblies of FIG. 9A after having been secured to the tissue by the end effector of FIG. 3.

A series of staples (47) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (12) is pulled away from tissue ($T_1$, $T_2$) after deploying staples (47) and buttress assemblies (110, 112), buttress assemblies (110, 112) disengage end effector such that buttress assemblies (110, 112) remain secured to tissue ($T_1$, $T_2$) with staples (47). Buttresses (110, 112) thus provides structural reinforcement to the lines of staples (47) formed in tissue ($T_1$, $T_2$). As can also be seen in FIG. 10, distally presented cutting edge (48) of firing beam (14) also cuts through a centerline of buttress tissue assemblies (110, 112), separating each buttress assembly (110, 112) into a corresponding pair of sections, such that each section remains secured to a respective severed region of tissue ($T_1$, $T_2$).

C. Exemplary Buttress Applier Cartridge with Active Retainer Arms

Figure 11:
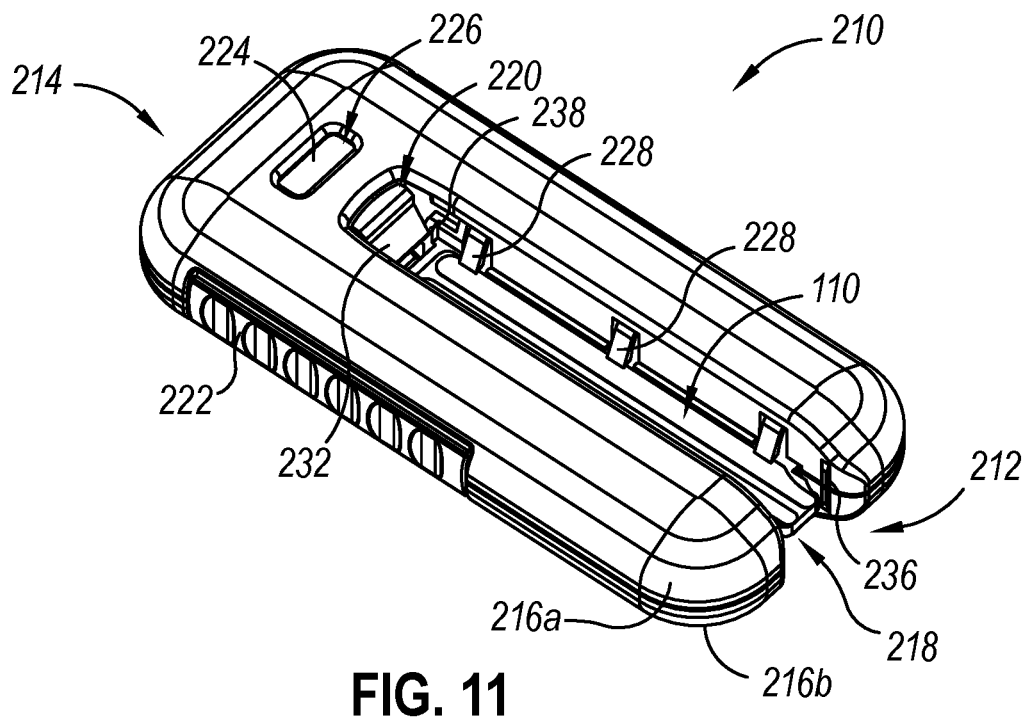
FIG. 11 depicts a perspective view of an exemplary buttress applier cartridge that may be used to carry and apply the buttress assemblies of FIG. 8.
Figure 12:
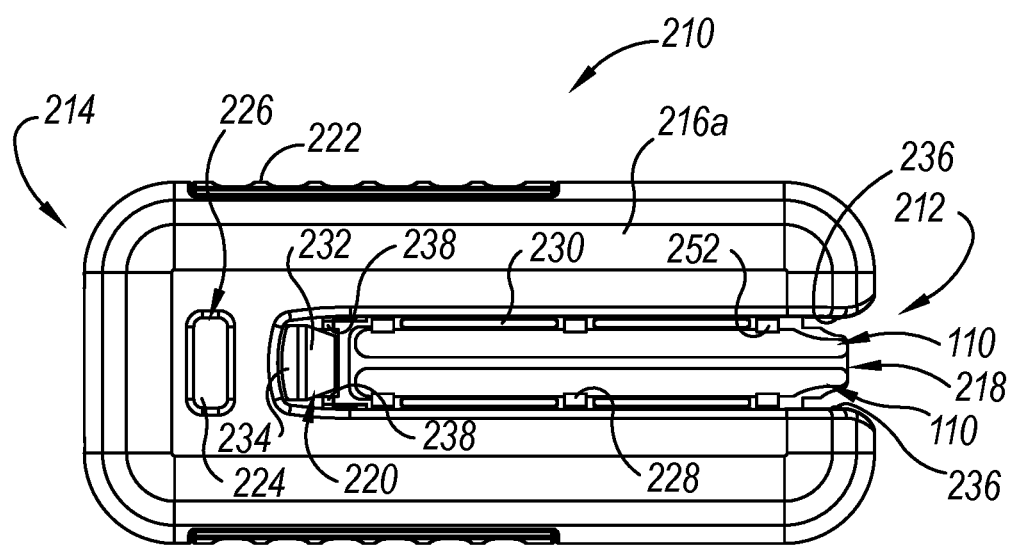
FIG. 12 depicts a top plan view of the buttress applier cartridge of FIG. 11.

Because end effector (12) of surgical instrument (10) may be actuated multiple times during a single surgical procedure, it may be desirable to enable an operator to repeatedly and easily load buttress assemblies (110, 112) onto end effector jaws (16, 18) during that single surgical procedure. FIGS. 11-13B show an exemplary buttress applier cartridge (210) (also referred to as a "buttress applicator") that may be used to support, protect, and apply adjunct material, such as buttress assemblies (110, 112), to end effector (12). As best seen in FIGS. 11-12, cartridge (210) of this example comprises an open end (212) and a closed end (214). Open end (212) is configured to receive end effector (12) as will be described in greater detail below. Cartridge (210) further includes a first housing (216a) and a second housing (216b), which each collectively generally define a "U" shape to present open end (212). A platform (218) and a sled retainer (220) are interposed between first and second housings (216a, 216b).

Platform (218) of the present example is configured to support a pair of buttress assemblies (110) on one side of platform (218) and another pair of buttress assemblies (112) on the other side of platform (218). Platform (218) is exposed in recesses that are formed between the prongs of the "U" configuration of first and second housings (216a, 216b). Each buttress assembly (110, 112) is provided in a respective pair of portions that are separated to avoid spanning across slots (42, 49) of anvil (18) and staple cartridge (37), respectively, though platform (218) may just as easily support wide versions of buttress assemblies (110, 112) that unitarily span across slots (42, 49) of anvil (18) and staple cartridge (37), respectively. More specifically, the outer edges of platform (218) include retention features (230) in the form of ridges that further engage first and second housings (216a, 216b) to prevent platform (218) from sliding relative to first and second housings (216a, 216b).

First and second housings (216a, 216b) include integral gripping features (222) and indicator plates (224) positioned to correspond with windows (226) formed in first and second housings (216a, 216b), such that indicator plates (224) are visible through windows (226) at different times. Arms (228) of the present example are configured to selectively secure buttress assemblies (110, 112) to platform (218). In the present example, arms (228) are resilient and are thus configured to resiliently bear against buttress assemblies (110, 112), thereby pinching buttress assemblies (110, 112) against platform (218). Buttress applier cartridge (210) includes a pair of tapered cam surfaces (232) and a respective pair of housing engagement features (234) positioned to engage corresponding surfaces of first and second housings (216a, 216b). First and second housings (216a, 216b) include proximal guide features (236) and distal guide features (238) configured to assist in providing proper alignment of end effector (40) with cartridge (210).

Figure 13A:
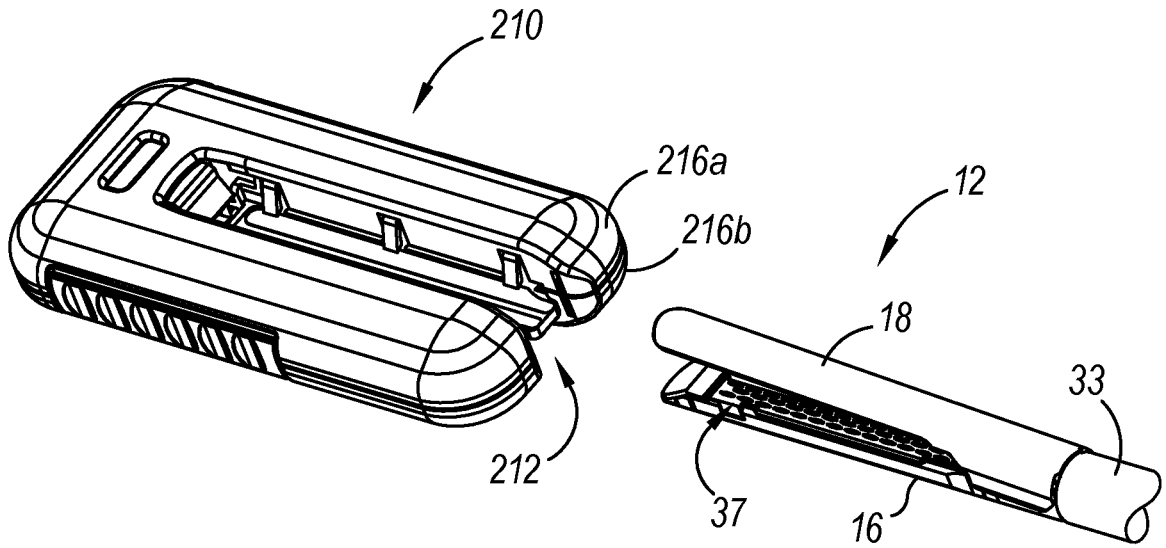
FIG. 13A depicts a perspective view of the end effector of FIG. 3 and the buttress applier cartridge of FIG. 11, showing the end effector and the buttress applier cartridge being aligned with one another.
Figure 13B:
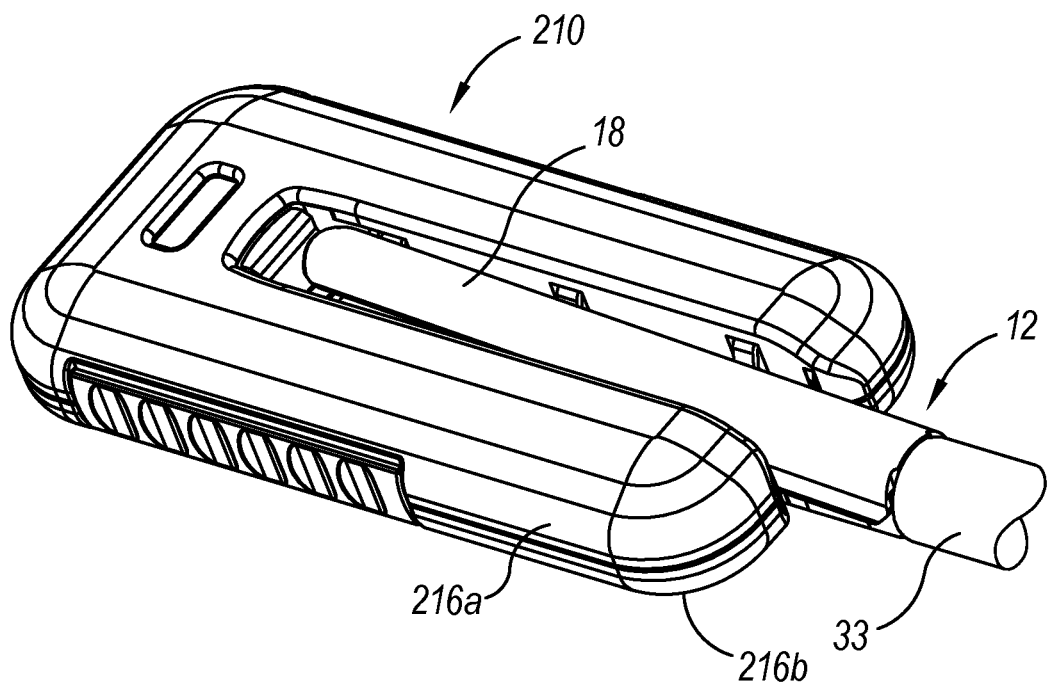
FIG. 13B depicts a perspective view of the end effector of FIG. 3 and the buttress applier cartridge of FIG. 11, with the end effectors jaws closed on a platform of the buttress applier cartridge.

FIG. 13A shows cartridge (210) in a configuration where retainer arms (228) are positioned to hold buttress assemblies (110, 112) against platform (218); while FIG. 13B shows cartridge (210) in a configuration where retainer arms (228) are positioned to release buttress assemblies (110, 112) from platform (218). While FIGS. 13A-13B only show buttress assembly (110) on platform (218), buttress assembly (112) would be retained on and released from platform (218) in an identical fashion. To use cartridge (210) to load end effector (12), the operator would first position cartridge (210) and end effector (12) such that end effector is aligned with open end (212) of cartridge (210) as shown in FIG. 13A. The operator would then advance end effector (12) distally, and/or advance cartridge (210) proximally, to position platform (218) and buttress assemblies (110, 112) between anvil (18) and staple cartridge (37) as shown in FIG. 13B. Closure trigger (26) of instrument (10) is then squeezed by the operator to close end effector jaws (16, 18) on platform (218), thereby adhesively attaching buttress assemblies (110, 112) to anvil (18) and staple cartridge (37), and simultaneously depressing cam surface (232). Depression of cam surface (232) actuates retainer arms (228) laterally outwardly to thereby release buttress assemblies (110, 112) from platform (218), such that end effector jaws (16, 18) may be disengaged from platform (218) while buttress assemblies (110, 112) remain adhered to anvil (18) and staple cartridge (37).

III. EXEMPLARY ALTERNATIVE APPLICATOR DEVICES AND RELATED METHODS OF APPLYING A BUTTRESS TO A SURGICAL STAPLER END EFFECTOR

In some instances, it may be desirable to provide an applicator device that is configured to apply a staple reinforcing adjunct element to one or both jaws of a surgical stapler end effector while the jaws remain in an open state, or otherwise without closing the jaws via actuation of the stapler's end effector closure system, such as via actuation of closure trigger (26) of surgical stapler (10). The exemplary applicator devices described below provide such functionality, such that each applicator device is configured to be manipulated relative to an end effector to apply an adjunct element to one or both jaws without requiring actuated closure of the jaws like that shown in FIGS. 13A-13B described above.

It will be appreciated that any of the exemplary applicator devices described below may be configured to apply an adjunct element in the form of a buttress, such as buttress assemblies (110, 112) described above, or a tissue thickness compensator, for example of the type disclosed in U.S. Pat. Pub. No. 2012/0080336, entitled "Staple Cartridge Comprising Staples Positioned Within A Compressible Portion Thereof," published Apr. 5, 2012 and now abandoned, the disclosure of which is incorporated by reference herein. Additionally, application of a staple reinforcement element to an end effector jaw may be achieved with adhesive features as described above and/or with mechanical coupling features, for example of the type disclosed in U.S. Pat. No. 7,665,646, entitled "Interlocking Buttress Material Retention System," issued Feb. 23, 2010, the disclosure of which is incorporated by reference herein. Furthermore, any of the exemplary applicator devices described below may be suitably constructed for a single use or for multiple uses.

A. First Exemplary Alternative Applicator Device

Figure 14A:
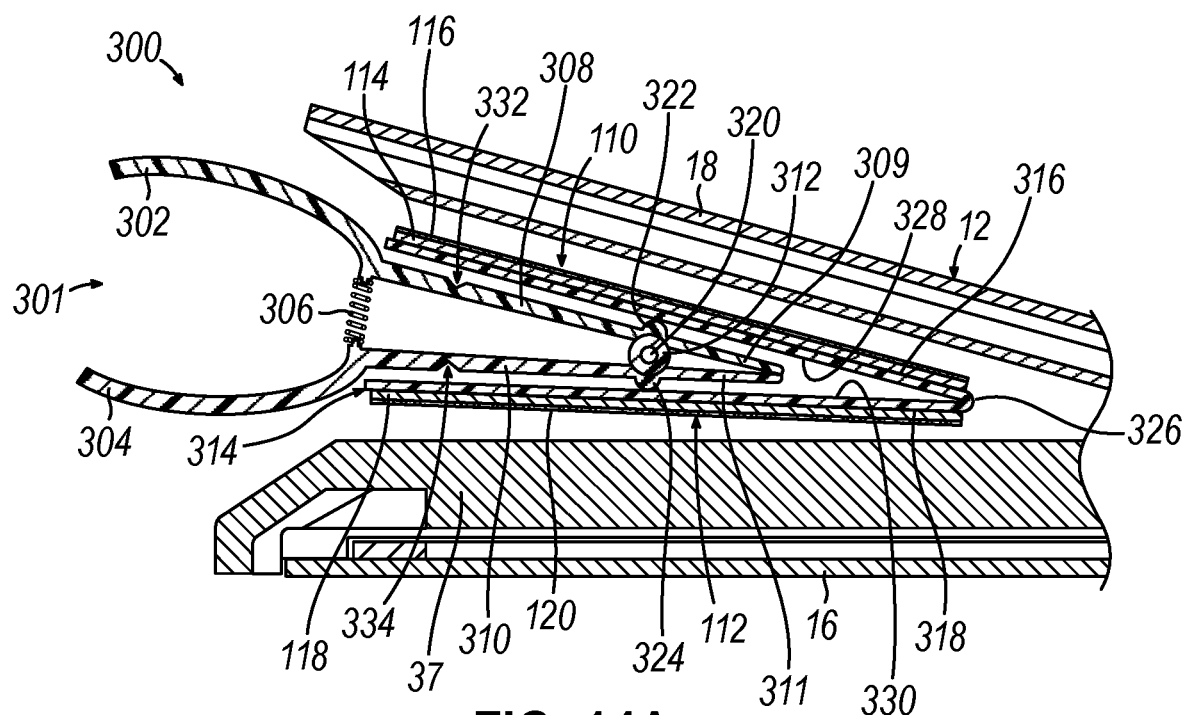
FIG. 14A depicts a side cross-sectional view of a first exemplary alternative applicator device, the buttress assembly of FIG. 8 applied to the applicator device, and the end effector of FIG. 3, showing the applicator device in a non-expanded state.
Figure 14B:
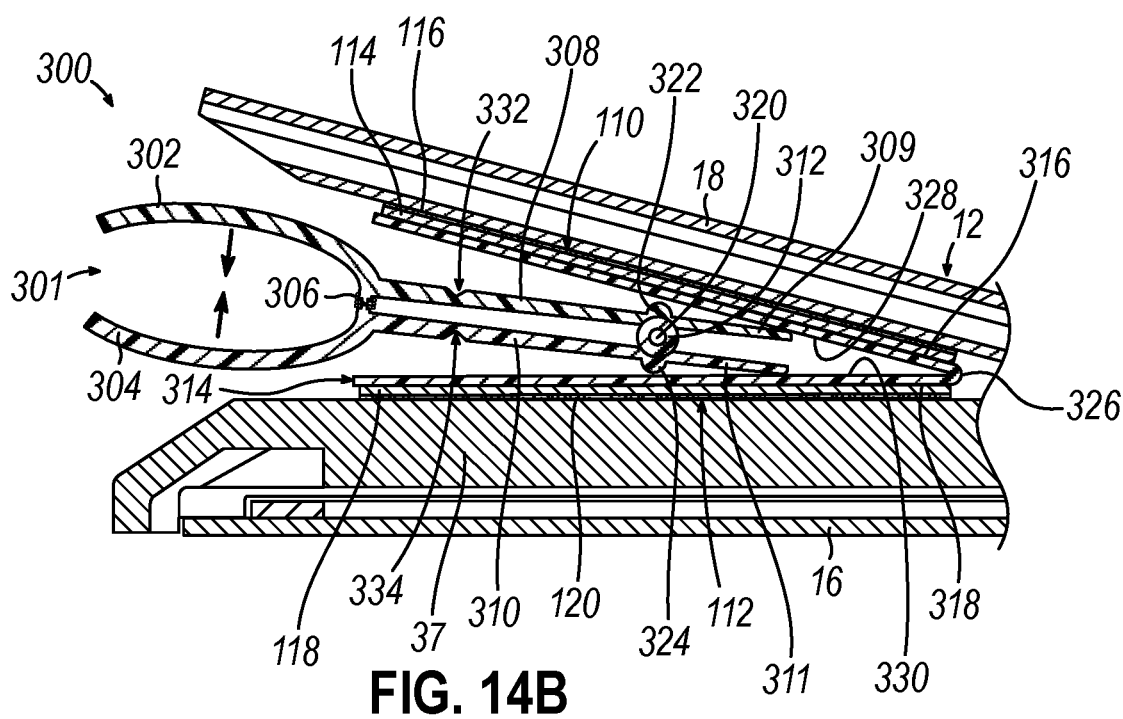
FIG. 14B depicts a side cross-sectional view of the applicator device of FIG. 14A, the buttress assembly of FIG. 8, and the end effector of FIG. 3, with the applicator device in an expanded state for securing the buttress assembly to the end effector.

FIGS. 14A-14B show a first exemplary alternative applicator device (300) that is configured to apply an adjunct material (e.g., buttress assembly (110, 112) or a tissue thickness compensator) to a jaw (e.g., lower jaw (16) or anvil (18)) of end effector (12) of surgical stapler (10). Applicator device (310) adjusts for the thickness of anvil (18) or lower jaw (16) allowing applicator device (310) to suitably apply adjunct material to both anvil (18) and lower jaw (16) separately. As shown in FIG. 14A, applicator device (300) includes an expansion mechanism (301) and a contact structure shown as an expandable wedge (314). Expansion mechanism (301) of the present example includes handles (302, 304), a compression spring (306), and applicator arms (308, 310).

Wedge (314) of the present example is configured to support a pair of buttress assemblies (110) on one side of wedge (314) and another pair of buttress assemblies (112) on the reverse side of wedge (314). Each buttress assembly (110, 112) is provided in a respective pair of portions that are separated to avoid spanning across slots (42, 49) of anvil (18) and staple cartridge (37) (see, FIG. 3), respectively, though wedge (314) may just as easily support wide versions of buttress assemblies (110, 112) that unitarily span across slots (42, 49) of anvil (18) and staple cartridge (37), respectively. Applicator arms (308, 310) are separated by a pivot member (shown as pin (312)) configured to rotatably couple with applicator arms (308, 310). Applicator device (300) may therefore resemble reverse pliers, that is, compression spring (306) is configured to provide a force biasing handles (302, 304) away from each other, thereby biasing distal portions (309, 311) of applicator arms (308, 310) toward each other via pivoting rotation about axis (320) provided by pin (312). Wedge (314) is configured to contact applicator arms (308, 310) via contact members (322, 324); however, contact members (322, 324) are merely optional and may be omitted in some versions. Further, wedge (314) includes first applicator surface (316) and second applicator surface (318) coupled together at resilient pivoting point (326).

First and second applicator surfaces (316, 318) are each configured to apply adjunct material to end effector (12) of stapling instrument (10). More specifically, first applicator surface (316) is configured to accept buttress assembly (110) thereon for application onto pivotable anvil (18), and second applicator surface (318) is configured to accept buttress assembly (112) thereon for application on to lower jaw (16). Particularly, buttress assembly (110) is placed onto first applicator surface (316) such that upper adhesive layer (116) is facing outwardly away from first applicator surface (316), and buttress assembly (112) is placed onto second applicator surface (318) such that lower adhesive layer (120) is facing outwardly away from second applicator surface (318), thereby allowing first and second adhesive layers (116, 120) to adhere to pivotable anvil (18) and lower jaw (16), respectively, upon application of buttress assemblies (110, 112) by applicator device (300). In some versions, first and second applicator surfaces (316, 318) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator surfaces (316, 318) prior to buttress assemblies (110, 112) being applied to pivotable anvil (18) and lower jaw (16), respectively. However, various suitable methods and structures for securely and removably positioning buttress assemblies (110, 112) on applicator surfaces (316, 318) are also envisioned. In some versions, a user utilizing a separate device (not shown) may initially apply one or both buttress assemblies (110, 112) to applicator surfaces (316, 318).

FIG. 14B shows the adjunct material being secured onto stapling surfaces of pivotable anvil (18) and lower jaw (16) of end effector (12). As described above, the adjunct material may include buttress assemblies (110, 112), tissue thickness compensators, or other suitable materials. The stapling surface is intended to include upper deck (72) of staple cartridge (37) that includes staple apertures (50) or a contact surface (52) of anvil (18) that includes staple forming pockets (53) as shown in FIG. 3. It is also envisioned that anvil (18) may be disposed on the lower jaw and the staple cartridge (37) may be disposed on the upper jaw.

As shown in FIG. 14B, once buttress assemblies (110, 112) are positioned on applicator surfaces (316, 318), handles (302, 304) of applicator device (300) are squeezed together to thereby compress spring (306) and pivot applicator arms (308, 310) about axis (320). As handles (302, 304) transition closer together, distal portions (309, 311) of applicator arms (308, 310) transition away from each other and contact inward-facing surfaces (328, 330) of applicator arms (308, 310) to spread (i.e., separate) applicator arms (308, 310) in opposing directions via resilient pivoting point (326) until buttress assemblies (110, 112) adhere to pivotable anvil (18) and lower jaw (16), respectively. More specifically, wedge (314) defines a distal opening angle that increases as applicator arms (308, 310) of wedge (314) spread, thus advancing each applicator arm (308, 310) toward the respective jaw of end effector (12).

Thereafter, handles (302, 304) may be released by the user thereby reversing the pivoting motion of applicator arms (308, 310), disengaging from buttress assemblies (110, 112) as buttress assemblies (110, 112) remain adhered to pivotable anvil (18) and lower jaw (16). Applicator device (300) may thereafter be removed.

In some versions, a break-away feature may be desired to ensure the applicator device (300) does not apply too much pressure to end effector (12) while applying buttress assemblies (110, 112). For example, one or more breakaway features, such as notches (332, 334) can be included on applicator arms (308, 310). In the illustrated example, notches (332, 334) are included between handles (302, 304) and pin (312), and arms (308, 310) are configured to break at notches (332, 334), respectively, if arms (408, 410)

experience force above a predetermined limit while applying buttress assemblies (110, 112).

B. Second Exemplary Alternative Applicator Device

Figure 15A:
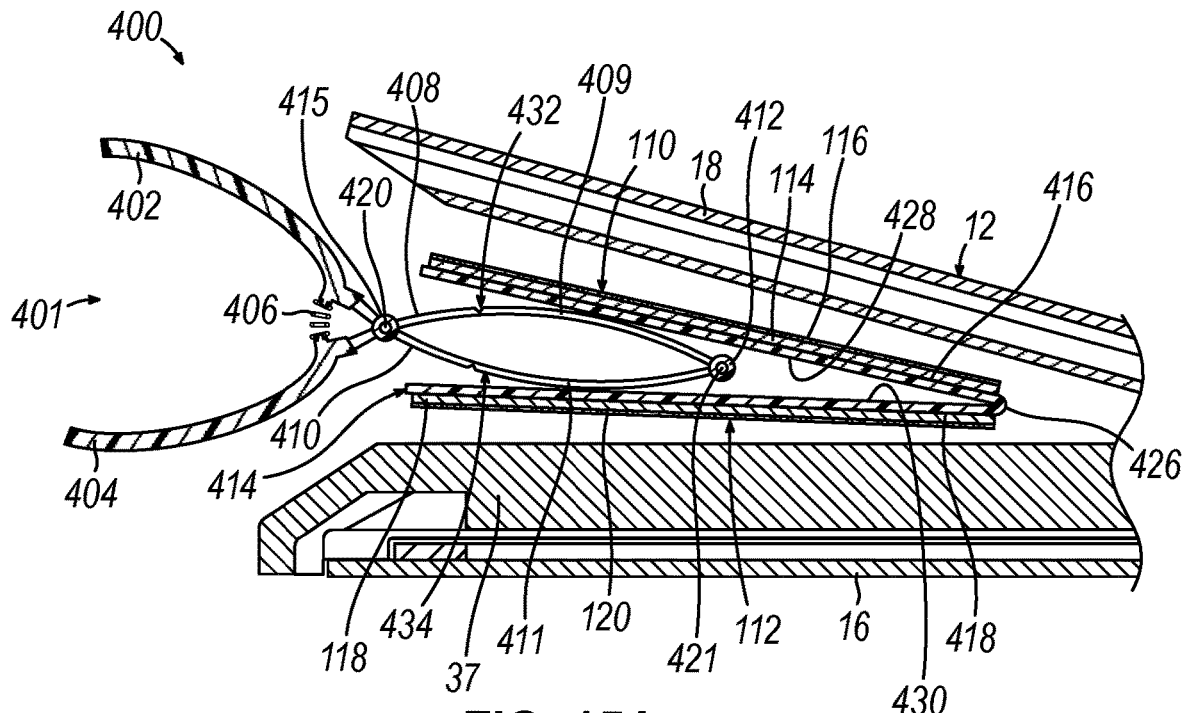
FIG. 15A depicts a side cross-sectional view of a second exemplary alternative applicator device, the buttress assembly of FIG. 8 applied to the applicator device, and the end effector of FIG. 3, showing the applicator device in a non-expanded state.
Figure 15B:
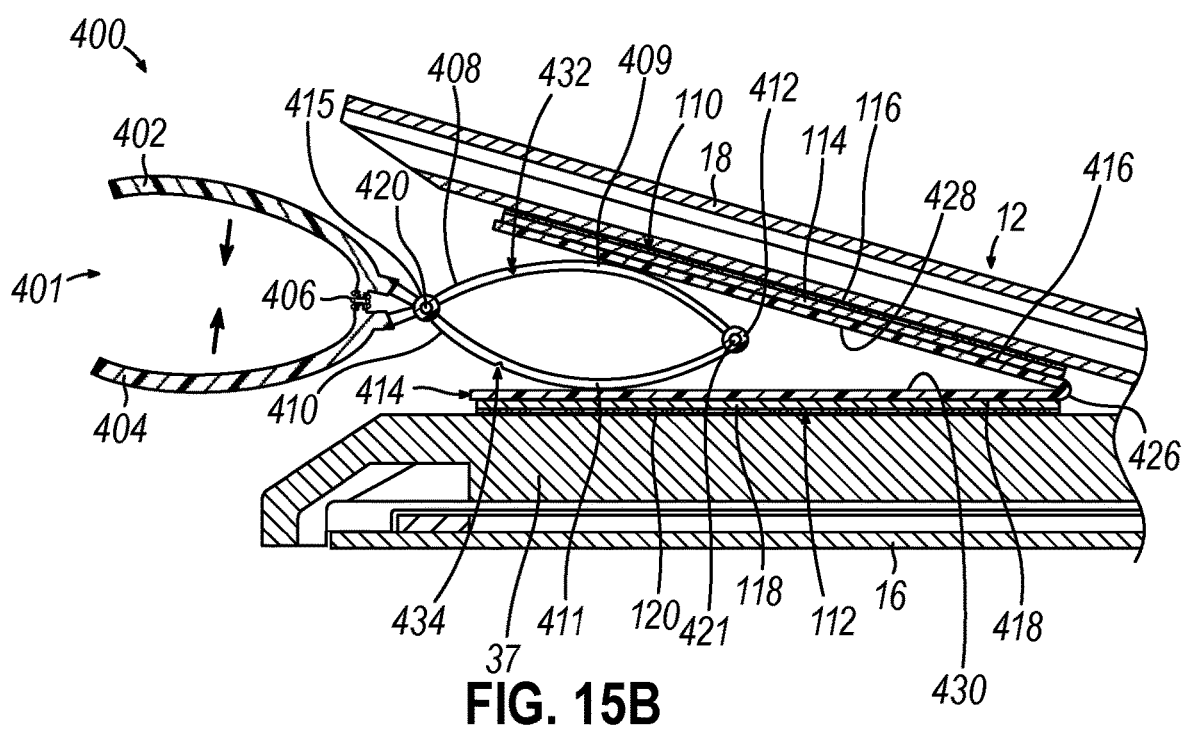
FIG. 15B depicts a side cross-sectional view of the applicator device of FIG. 15A, the buttress assembly of FIG.

FIGS. 15A-15B show a second exemplary alternative applicator device (400) that is configured to apply an adjunct material to a jaw (e.g., lower jaw (16) or anvil (18)) of end effector (12) of surgical stapler (10). Applicator device (410) adjusts for thickness of anvil (18) or lower jaw (16) allowing applicator device (410) to suitably apply adjunct material to anvil (18) and lower jaw (16). As a result, the application of buttress assembly (112) using applicator device (410) to lower jaw (16) that includes staple cartridge (37) may be similar to the application of buttress assembly (300) described above. As shown in FIG. 15A, applicator device (400) includes an expansion mechanism (401) and a contact structure shown as expandable wedge (414). Expansion mechanism (401) of the present example includes handles (402, 404), a compression spring (406), and applicator arms (408, 410).

Applicator arms (408, 410) are coupled together at first and second pivot members (shown as pins (411, 412)). Compression spring (406) is configured to provide a force biasing handles (402, 404) away from each other, thereby biasing flexible central portions (409, 411) of applicator arms (408, 410) toward each other via pivoting rotation about pivot axes (420, 421) provided by pins (411, 412). Wedge (414) of the present example is configured to support a pair of buttress assemblies (110) on one side of wedge (414) and another pair of buttress assemblies (112) on the reverse side of wedge (414). Each buttress assembly (110, 112) is provided in a respective pair of portions that are separated to avoid spanning across slots (42, 49) of anvil (18) and staple cartridge (37) (see, FIG. 3), respectively, though wedge (414) may just as easily support wide versions of buttress assemblies (110, 112) that unitarily span across slots (42, 49) of anvil (18) and staple cartridge (37), respectively. Wedge (414) is configured to contact applicator arms (408, 410) along flexible central portions (409, 411) of applicator arms (408, 410). Further, wedge (414) includes first applicator surface (416) and second applicator surface (418) coupled together at resilient pivoting point (426). In some versions, flexible central portions (409, 411) may be secured to applicator arms (408, 410).

First and second applicator surfaces (416, 418) are each configured to apply adjunct material to end effector (12) of stapling instrument (10). More specifically, first applicator surface (416) is configured to accept buttress assembly (110) thereon for application onto pivotable anvil (18), and second applicator surface (418) is configured to accept buttress assembly (112) thereon for application on to lower jaw (16). Particularly, buttress assembly (110) is placed onto first applicator surface (416) such that upper adhesive layer (116) is facing outwardly away from first applicator surface (416), and buttress assembly (112) is placed onto second applicator surface (418) such that lower adhesive layer (120) is facing outwardly away from second applicator surface (418), thereby allowing first and second adhesive layers (116, 120) to adhere to pivotable anvil (18) and lower jaw (16), respectively, upon application of buttress assemblies (110, 112) by applicator device (400). In some versions, first and second applicator surfaces (416, 418) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator surfaces (416, 418) prior to buttress assemblies (110, 112) being applied to pivotable anvil (18) and lower jaw (16), respectively. However, various suitable methods and structures for securely and removably positioning buttress assemblies (110, 112) on applicator surfaces (416, 418) are also envisioned. In some versions, a user utilizing a separate device (not shown) may initially apply one or both buttress assemblies (110, 112) to applicator surfaces (416, 418).

FIG. 15B shows the adjunct material being secured onto stapling surfaces of pivotable anvil (18) and lower jaw (16) of end effector (12). Once buttress assemblies (110, 112) are positioned on applicator surfaces (416, 418), handles (402, 404) of applicator device (400) are squeezed together to thereby compress spring (406) and pivot applicator arms (408, 410) about axes (420, 421). As handles (402, 404) transition closer together, flexible central portions (409, 411) of applicator arms (408, 410) deflect away from each other to become more convex to contact inward-facing surfaces (428, 430) of applicator arms (408, 410) and spread applicator arms (408, 410) in opposing directions via resilient pivoting point (426) until buttress assemblies (110, 112) adhere to pivotable anvil (18) and lower jaw (16), respectively. Thereafter, handles (402, 404) may be released by the user thereby reversing the pivoting motion of applicator arms (408, 410), disengaging from buttress assemblies (110, 112) as buttress assemblies (110, 112) remain adhered to pivotable anvil (18) and lower jaw (16). End effector (12) may thereafter be removed from applicator device (400).

In some versions, a break-away feature may be desired to ensure the applicator device (400) does not apply too much pressure to end effector (12) while applying buttress assemblies (110, 112). For example, one or more breakaway features, such as notches (432, 434) can be included on applicator arms (408, 410). In the illustrated example, notches (432, 434) are included between handles (402, 404) and pin (412), and arms (408, 410) are configured to break at notches (432, 434), respectively, if arms (408, 410) experience force above a particular limit while applying buttress assemblies (110, 112).

C. Third Exemplary Alternative Applicator Device

FIGS. 16A-16C show a third exemplary alternative applicator device (500) that is configured to apply an adjunct material to a jaw (e.g., lower jaw (16)) of end effector (12) of surgical stapler (10). As best seen in FIG. 16A, applicator device (500) of this example may resemble buttress applier cartridge (210) (see, FIG. 11), except for the differences described below. Specifically, applicator device (500) comprises a body (502) defining an open end (504) and a closed end (506). Open end (504) is configured to receive end effector (12) as will be described in greater detail below. Applicator device (500) further includes a first housing (508a) and a second housing (508b), which each collectively generally define a "U" shape to present open end (504). A contact structure in the form of an expandable wedge (510) is interposed between first and second housings (508a, 508b). Wedge (510) of the present example is configured to support a pair of buttress assemblies (110) on one side (511a) of wedge (510) and another pair of buttress assemblies (112) on the other side (511b) of wedge (510). Wedge (510) is exposed in recesses that are formed between the prongs of the "U" configuration of first and second housings (508a, 508b). Each buttress assembly (110, 112) is provided in a respective pair of portions that are separated to avoid spanning across slots (42, 49) of anvil (18) and staple cartridge (37) (see, FIG. 3), respectively, though wedge (510) may just as easily support wide versions of buttress assemblies (110, 112) that unitarily span across slots (42, 49) of anvil (18) and staple cartridge (37), respectively.

As shown in FIG. 16B, applicator device (500) further includes a fluid connector (512) and a fluid conduit (514) fluidly coupled with wedge (510). Fluid connector (512) is positioned at closed end (506) of cartridge body (502) and configured to couple with an applicator expansion mechanism in the form of a pump (518). In some versions, pump (518) may be an inflatable, flexible balloon filled with air, while in other versions pump (518) may be a similar pumping device pre-filled with a liquid, such as water or saline, that is actuatable by a user to expel the liquid therefrom. Fluid connector (512) may be any suitable fluid-tight connector known in the art, such as a luer or snap-fit connector, that is configured to couple with a complementary connector (520) of pump (518). When coupled together, fluid connectors (512, 520) define a lumen configured to communicate a fluid (e.g., air, water, saline, etc.) from pump (518) through fluid conduit (514) in a direction toward open end (504) of cartridge body (502). As will be described in greater detail below, fluid conduit (514) is configured to couple with wedge (510) such that, upon receiving fluid from fluid conduit (514), wedge (510) transitions from a first state (see, FIG. 16B) to a second state (see, FIG. 16C) to expand opposing sides (511a, 511b) of wedge (510) in opposing outward directions, each away from longitudinal axis (534), to thereby apply buttress assemblies (110, 112) to pivotable anvil (18) and lower jaw (16). In some versions, fluid connector (520) or fluid conduit (514) includes a check valve (528) to ensure fluid pressure remains constant within fluid conduit (514) until the user disengages pump (518) from cartridge body (502).

Wedge (510) includes first and second contact members in the form of first and second applicator surfaces (522, 524) each configured to apply adjunct material to end effector (12) of stapling instrument (10). Particularly, first side (511a) of wedge (510) includes first applicator surface (522) and second side (511b) of wedge (510) includes second applicator surface (524). First and second applicator surfaces (522, 524) join at point (526) of wedge (510) such that surfaces (522, 524) are movably coupled with one another. Wedge (510) may be comprised of any one material or a plurality of materials providing sufficient rigidity at each applicator surface (522, 524) to both accept and apply buttress assemblies (110, 112) while also providing sufficient flexibility to repeatedly expand and contract as pressure is applied from pump (518) to expand each applicator surface (522, 524) outwardly to apply buttress assemblies (110, 112). In some examples, wedge (510) may be comprised of an elastomeric material (e.g., silicone) having a hollow interior that is biased toward a collapsed or flattened configuration, as shown in FIGS. 16A and 16B, and which is configured to expand as it is filled with fluid.

As noted above, first applicator surface (522) is configured to accept buttress assembly (110) thereon for application onto pivotable anvil (18), and second applicator surface (524) is configured to accept buttress assembly (112) thereon for application on to lower jaw (16). Buttress assembly (110) is placed onto first applicator surface (522) such that upper adhesive layer (116) is facing outwardly away from first applicator surface (522), and buttress assembly (112) is placed onto second applicator surface (524) such that lower adhesive layer (120) is facing outwardly away from second applicator surface (524), thereby allowing first and second adhesive layers (116, 120) to adhere to pivotable anvil (18) and lower jaw (16), respectively, upon application of buttress assemblies (110, 112) by applicator device (500). In some versions, first and second applicator surfaces (522, 524) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator surfaces (522, 524) prior to buttress assemblies (110, 112) being applied to pivotable anvil (18) and lower jaw (16), respectively. However, various suitable methods and structures for securely and removably positioning buttress assemblies (110, 112) on applicator surfaces (522, 524) are also envisioned. In some versions, a user utilizing a separate device (not shown) may initially apply one or both buttress assemblies (110, 112) to applicator surfaces (522, 524).

FIG. 16C shows the adjunct material being secured onto stapling surfaces of pivotable anvil (18) and lower jaw (16) of end effector (12). Once buttress assemblies (110, 112) are positioned on applicator surfaces (522, 524), end effector (12) is placed into position for application of buttress assemblies (110, 112), and pump (518) is coupled with cartridge body (502), a user may then grasp and squeeze pump (518) one or more times to expel fluid (e.g., air, water, saline, etc.) from pump (518) through fluid conduit (514). The fluid communicating through fluid conduit (514) pressurizes to expand wedge (510), which thereby inflates and spreads applicator surfaces (522, 524) in opposite outward directions. As applicator surfaces (522, 524) spread apart in opposite outward directions, buttress assemblies (110, 112) may be applied to end effector (12) without requiring any actuation of pivotable anvil (18) or lower jaw (16).

Thereafter, fluid pressure applied to wedge (510) within fluid conduit (514) may be released by the user by disengaging pump (518), thereby releasing the fluid from fluid conduit (414). Releasing the fluid from fluid conduit (414) may function to reverse the spreading of applicator surfaces (522, 524), disengaging from buttress assemblies (110, 112) as buttress assemblies (110, 112) remain adhered to pivotable anvil (18) and lower jaw (16). End effector (12) may thereafter be removed from applicator device (500).

D. Fourth Exemplary Alternative Applicator Device

FIG. 17 shows a fourth exemplary alternative applicator device (600) that is configured to apply an adjunct material to a jaw (e.g., lower jaw (16)) of end effector (12) of surgical stapler (10). Applicator device (600) is configured with the same structures and functionality as applicator device (500), except for the differences described below. As an alternative to pump (518) of applicator device (500), applicator device (600) is configured to accept a fluid (602) (e.g., air, water, saline, etc.) injected using an applicator expansion mechanism in the form of a syringe (604) or other similar fluid injection device known and used in the art. To operate applicator device (600) to apply buttresses (110, 112), that is, to inflate expandable wedge (614) and extend applicator surfaces (622, 624) outwardly, a user may couple syringe (604) to fluid connector (606) of cartridge body (608) and actuate the plunger (610) in a distal longitudinal direction along axis (612). To retract applicator surfaces (622, 624) inwardly, the user may retract plunger (610) proximally along longitudinal axis (612) to thereby retract fluid (602) out of wedge (614) via fluid conduit (620) and back into syringe (604).

E. Fifth Exemplary Alternative Applicator Device

FIGS. 18A-18C show a fifth exemplary alternative applicator device (700) that is configured to apply an adjunct material to a jaw (e.g., lower jaw (16)) of end effector (12) of surgical stapler (10). Applicator device (700) is configured with the same structures and functionality as applicator devices (500, 600), except for the differences described below. As an alternative to pump (518) of applicator device (500) and to syringe (604) of applicator device (600), applicator device (700) is configured to accept compressed gas (702) (e.g., air, CO2, etc.) injected using an applicator expansion mechanism in the form of a canister (704) or other similar injection device known and used in the art. To operate applicator device (700) to apply buttresses (110, 112), that is, to inflate wedge (714) and extend applicator surfaces (722, 724) of wedge (714) outwardly, a user may couple canister (704) to fluid conduit (706) of cartridge body (708) via fluid connector (710). Canister (704) may therefore include a connector (shown as threads (712)) configured to couple with fluid connector (710), and a thin seal (716) configured to be punctured by a sharp tip (730) formed by the proximal end (728) of fluid conduit (706) thereby releasing the compressed gas (702) from the canister outlet (718).

In the illustrated example, a user couples canister (704) with cartridge body (708) by threading connector (712) of canister (704) into fluid connector (710), thereby translating canister (704) in a distal longitudinal direction along axis (720). Once canister (704) is adequately coupled with cartridge body (708) and buttress assemblies (110, 112) have been applied to applicator surfaces (722, 724) of wedge (714), end effector (12) may be positioned for application, as shown in FIG. 18B. At this stage, seal (718) has been positioned adjacent sharp tip (730) of rigid puncture mechanism (740), whereby the proximal end of fluid conduit (706) is disposed within a hollow portion (744) defined at the proximal end of rigid puncture mechanism (740). Seal (742) prevents fluid leakage where fluid conduit (706) inserts into the hollow portion (744) of rigid puncture mechanism (740). To expel the compressed gas (702) from canister (704), anvil portions (90a, 90b) (see, FIGS. 3, 6, 18B, and 18C) are configured to press against distal end (746) of rigid puncture mechanism (740) near distal tip (726) of wedge (714), thereby translating rigid puncture mechanism (740) proximally (i.e., toward canister (704)). As rigid puncture mechanism (740) is translated proximally, sharp tip (730) punctures through seal (718) and permits compressed gas (702) to flow distally through the lumen defined by fluid conduit (706).

In alternative versions, wedge (714) may be slideably secured along the longitudinal axis (720) relative to cartridge body (708), and sharp tip (730) may be formed integrally as a proximal portion of fluid conduit (706). As such, seal (716) may be punctured by fluid conduit (706) and buttress assemblies (110, 112) may therefore be applied by a user simply threading canister (704) into fluid connector (710).

Thereafter, pressure applied to rod (732) within fluid conduit (706) may be released by the user by disengaging canister (704), thereby releasing the gas from fluid conduit (706). Releasing the gas from fluid conduit (706) may function to reverse the spreading or pivoting motion of applicator arms (722, 724), disengaging from buttress assemblies (110, 112) as buttress assemblies (110, 112) remain adhered to pivotable anvil (18) and lower jaw (16). End effector (12) may thereafter be removed from applicator device (700).

F. Sixth Exemplary Alternative Applicator Device

FIGS. 19A-19B show a sixth exemplary alternative applicator device (800) that is configured to apply an adjunct material to a jaw (e.g., lower jaw (16)) of end effector (12) of surgical stapler (10). Applicator device (800) includes a contact structure having first and second applicator arms (802, 804) configured to couple with an applicator expansion mechanism in the form of a rotary actuator (806). Applicator arms (802, 804) of the present example is configured to support a pair of buttress assemblies (110) on first applicator arm (802) and another pair of buttress assemblies (112) on second applicator arm (804) (first and second applicator arms (802, 804) collectively defining a wedge). Each buttress assembly (110, 112) is provided in a respective pair of portions that are separated to avoid spanning across slots (42, 49) of anvil (18) and staple cartridge (37) (see, FIG. 3), respectively, though applicator arms (802, 804) may just as easily support wide versions of buttress assemblies (110, 112) that unitarily span across slots (42, 49) of anvil (18) and staple cartridge (37), respectively. Applicator arms (802, 804) are coupled together using a pivot member (shown as pin (808)).

First and second applicator arms (802, 804) are each configured to apply adjunct material to end effector (12) of stapling instrument (10). More specifically, first applicator arm (802) is configured to accept buttress assembly (110) thereon for application onto pivotable anvil (18), and second applicator arm (804) is configured to accept buttress assembly (112) thereon for application on to lower jaw (16). Particularly, buttress assembly (110) is placed onto first applicator arm (802) such that upper adhesive layer (116) is facing outwardly away from first applicator arm (802), and buttress assembly (112) is placed onto second applicator arm (804) such that lower adhesive layer (120) is facing outwardly away from second applicator arm (804), thereby allowing first and second adhesive layers (116, 120) to adhere to pivotable anvil (18) and lower jaw (16), respectively, upon application of buttress assemblies (110, 112) by applicator device (800). In some versions, first and second applicator arms (802, 804) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator arms (802, 804) prior to buttress assemblies (110, 112) being applied to pivotable anvil (18) and lower jaw (16), respectively. However, various suitable methods and structures for securely and removably positioning buttress assemblies (110, 112) on applicator arms (802, 804) are also envisioned. In some versions, a user utilizing a separate device (not shown) may initially apply one or both buttress assemblies (110, 112) to applicator arms (802, 804).

As shown from the transition from FIG. 19A to FIG. 19B, applicator arms (802, 804) may be expanded in opposing outward directions by a user to thereby apply buttress assemblies (110, 112) to end effector (12). To expand applicator arms (802, 804) outwardly, a user grasps and rotates rotary actuator (806) in a first direction. Rotary actuator (806) is coupled with a threaded rod (810), and threaded rod (810) is rotatably coupled with each applicator arm (802, 804) via a hinged connector (shown as hinge pin (812)) and translatable legs (814, 816). First translatable leg (814) is rotatably coupled via a hinged connector (shown as hinge pin (822)) with an underside (818) of first applicator arm (802). Second translatable leg (816) is rotatably coupled via a hinged connector (shown as hinge pin (824)) with an underside (820) of second applicator arm (804). As rotary actuator (806) is rotated in the first direction, hinged connector (812) translates distally away from rotary actuator (806) toward distal end (826) of threaded rod (810). As such, as shown in FIG. 19B, translatable legs (814, 816) force applicator arms (802, 804) in opposing directions relative to each other to apply buttress assemblies (110, 112) to end effector (12). Thereafter, rotary actuator (806) may be rotated in an opposite, second direction which may function to reverse the spreading or pivoting motion of applicator arms (802, 804), disengaging from buttress assemblies (110, 112) as buttress assemblies (110, 112) remain adhered to pivotable anvil (18) and lower jaw (16). End effector (12) may thereafter be removed from applicator device (800).

G. Seventh Exemplary Alternative Applicator Device

FIGS. 20A-20C show a seventh exemplary alternative applicator device (900) that is configured to apply an adjunct material to a jaw (e.g., lower jaw (16)) of end effector (12) of surgical stapler (10). Applicator device (900) is configured with the same structures and functionality as applicator devices (500, 600, 700), except for the differences described below. As an alternative to pump (518) of applicator device (500), syringe (604) of applicator device (600), and canister (704) of applicator device (700), applicator device (900) comprises a contact structure in the form of a selectively expandable applicator (902) and an applicator expansion mechanism in the form of a removable clip (904). Applicator device (900) includes a cartridge body (916) defining a closed end (918) and an open end (920) and a pair of retention members (906, 908) operable to compress upper and lower surfaces (910, 912) of expandable applicator (902), as shown in FIGS. 20A and 20B. Expandable applicator (902) may be comprised of a compressible foam material that is biased to an expanded state. Further, expandable applicator (902) may be formed into a V-shaped wedge that provides a complementary shape to pivotable anvil (18) and lower jaw (16) that is operable to securely attach buttress assemblies (110, 112) to pivotable anvil (18) and lower jaw (16) when expandable applicator (902) expands between pivotable anvil (18) and lower jaw (16).

Upper and lower applicator surfaces (910, 912) are each configured to apply adjunct material to end effector (12) of stapling instrument (10). More specifically, upper applicator surface (910) is configured to accept buttress assembly (110) thereon for application onto pivotable anvil (18), and lower applicator surface (912) is configured to accept buttress assembly (112) thereon for application on to lower jaw (16). Particularly, buttress assembly (110) is placed onto upper applicator surface (910) such that upper adhesive layer (116) is facing outwardly away from upper applicator surface (910), and buttress assembly (112) is placed onto lower applicator surface (912) such that lower adhesive layer (120) is facing outwardly away from lower applicator surface (912), thereby allowing first and second adhesive layers (116, 120) to adhere to pivotable anvil (18) and lower jaw (16), respectively, upon application of buttress assemblies (110, 112) by applicator device (900). In some versions, upper and lower applicator surfaces (910, 912) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator surfaces (910, 912) prior to buttress assemblies (110, 112) being applied to pivotable anvil (18) and lower jaw (16), respectively. However, various suitable methods and structures for securely and removably positioning buttress assemblies (110, 112) on applicator surfaces (910, 912) are also envisioned. In some versions, a user utilizing a separate device (not shown) may initially apply one or both buttress assemblies (110, 112) to applicator surfaces (910, 912).

FIG. 20A shows expandable applicator (902) in an initial, compressed state with buttress assemblies (110, 112) installed thereon. Further, retention members (906, 908) of clip (904) ensure expandable application (902) remains in a compressed state until end effector (12) is positioned for application of buttress assemblies (110, 112). FIG. 20B shows end effector (12) being translated into position to apply buttress assemblies (110, 112). Upon translating end effector (12) into position, tip (922) of pivotable anvil (18) is configured to contact a portion (914) of clip (904), thereby translating clip (904) toward closed end (918) of cartridge body (916). As clip (904) is translated, such as by sliding along the surface of cartridge body (916), retention members (906, 908) release from their positions retaining expandable applicator (902) in the compressed state. FIG. 20C shows clip (904) removed and expandable applicator (902) in its expanded state whereby applicator surfaces (910, 912) expand in opposing directions relative to each other to apply buttress assemblies (110, 112) to end effector (12). End effector (12) may thereafter be removed from applicator device (900).

H. Eighth Exemplary Alternative Applicator Device

FIGS. 21A-22B show an eighth exemplary alternative applicator device (1000) that is configured to apply an adjunct material to a jaw (e.g., lower jaw (16)) of end effector (12) of surgical stapler (10). As best seen in FIG. 21A, applicator device (1000) of this example may resemble buttress applier cartridges (210, 500, 600, 700, 900), except for the differences described below. Specifically, applicator device (10000) comprises a cartridge body (1002) defining an open end (1004) and a closed end (1006). Open end (1004) is configured to receive end effector (12) as will be described in greater detail below. Applicator device (1000) further includes a first housing (1008a) and a second housing (1008b), which each collectively generally define a "U" shape to present open end (1004). A contact structure in the form of an expandable wedge (1010) is interposed between first and second housings (1008a, 1008b). Wedge (1010) of the present example is configured to support a pair of buttress assemblies (110) on first applicator arm (1020) and another pair of buttress assemblies (112) on the second applicator arm (1022). Wedge (1010) is exposed in recesses that are formed between the prongs of the "U" configuration of first and second housings (1008a, 1008b). Each buttress assembly (110, 112) is provided in a respective pair of portions that are separated to avoid spanning across slots (42, 49) of anvil (18) and staple cartridge (37) (see, FIG. 3), respectively, though wedge (1010) may just as easily support wide versions of buttress assemblies (110, 112) that unitarily span across slots (42, 49) of anvil (18) and staple cartridge (37), respectively.

Applicator device (1000) further includes an expansion mechanism defined collectively by an actuator member (1012), applicator actuation mechanism (1018), rod (1016), guide rod (1034), and applicator arms (1020, 1022), the expansion mechanism selectively operable to transition wedge (1010) between non-expanded and expanded states as explained in greater detail below. Actuator member (1012) is translatable longitudinally parallel to a guide rod (1034). Actuator member (1012) comprises one or more user grips (1014a, 1014b) coupled together internally through cartridge body (1002) and wedge (1010) via a rod (1016). Actuator member (1012) may further be configured to slide distally and proximally relative to closed end (1006) of cartridge body (1002). As will be described in greater detail below, actuator member (1012), or more particularly, rod (1016), is configured to couple with an applicator actuation mechanism (1018) (see, FIGS. 22A and 22B) such that, upon actuator member (1012) sliding distally relative to closed end (1006) of cartridge body (1002), applicator actuation mechanism (1018) slides distally over guide rod (1034) to transition applicator arms (1020, 1022) from a first non-expanded position (see, FIG. 22A) to a second expanded position (see, FIG. 22B). As will be described in greater detail below, applicator actuation mechanism (1018) is further coupled with first and second applicator arms (1020, 1022) of wedge (1010).

Wedge (1010) includes first and second applicator arms (1020, 1022) each configured to apply adjunct material to end effector (12) of stapling instrument (10). First and second applicator arms (1020, 1022) are coupled together at resilient pivoting point (1026) of wedge (1010). Wedge (1010) may be comprised of any one material or plurality of materials providing sufficient rigidity at each applicator arm (1020, 1022) to both accept and apply buttress assemblies (110, 112) while also providing sufficient flexibility to repeatedly flex at pivoting point (1026) as pressure is applied from applicator actuation mechanism (1018) to expand each applicator arm (1020, 1022) outwardly to apply buttress assemblies (110, 112). In some examples, wedge (1010) may be comprised of a resilient metal or metal alloy that is biased in a "closed" configuration, as shown in FIGS. 21A and 22A.

First applicator arm (1020) is configured to accept buttress assembly (110) thereon for application onto pivotable anvil (18), and second applicator arm (1022) is configured to accept buttress assembly (112) thereon for application on to lower jaw (16). Buttress assembly (110) is placed onto first applicator arm (1020) such that upper adhesive layer (116) is facing outwardly away from first applicator arm (1020), and buttress assembly (112) is placed onto second applicator arm (1022) such that lower adhesive layer (120) is facing outwardly away from second applicator arm (1022), thereby allowing first and second adhesive layers (116, 120) to adhere to pivotable anvil (18) and lower jaw (16), respectively, upon application of buttress assemblies (110, 112) by applicator device (1000). In some versions, first and second applicator arms (1022, 1024) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator arms (1020, 1022) prior to buttress assemblies (110, 112) being applied to pivotable anvil (18) and lower jaw (16), respectively. However, various other suitable methods and structures for securely and removably positioning buttress assemblies (110, 112) on applicator arms (1020, 1022) are also envisioned. In some versions, a user utilizing a separate device (not shown) may initially apply one or both buttress assemblies (110, 112) to applicator arms (1020, 1022).

FIGS. 21B and 22B show the adjunct material being secured onto stapling surfaces of pivotable anvil (18) and lower jaw (16) of end effector (12). Once buttress assemblies (110, 112) are positioned on applicator arms (1020, 1022), end effector (12) is placed into position for application of buttress assemblies (110, 112), a user may then grasp grips (1014a, 1014b) and slide actuator member (1012) distally relative to closed end (1006) of cartridge body (1002) to transition applicator actuation mechanism (1018) of wedge (1010) to the distal position. Distal end (1040) of applicator actuation mechanism (1018) abuts a compression spring (1032) disposed over a distal end (1042) of guide rod (1034). Spring (1032) is configured to apply proximal pressure against applicator actuation mechanism (1018) to counteract against the distal pressure provided by applicator actuation mechanism (1018). As such, when pressure is removed from applicator actuation mechanism (1018), such as when user slides actuator member (1012) proximally relative to closed end (1006), applicator actuation mechanism (1018) proximally translates back to its initial position as shown in FIGS. 21A and 22A.

As shown in FIGS. 22A and 22B, applicator actuation mechanism (1018) is moveably coupled to one end (1046) of one or more actuator arms (1044), and the opposing end (1048) of one or more actuator arms (1044) is coupled with wedge (1010). Particularly, each actuator arm (1044) is rotatably coupled with an interior or underside of first applicator arm (1020) or second applicator arm (1022). As such, applicator actuation mechanism (1018), actuator arms (1044), and wedge (1010) are configured to operate in similar fashion as an umbrella. That is, as applicator actuation mechanism (1018) translates in a distal direction over guide rod (1034), actuator arms (1044) force first and second applicator arms (1020, 1022) to spread apart in opposite outward directions via a hinged connection with applicator actuation mechanism (1018) at the first end (1046) of actuator arm (1044) and also via a hinged connection with an interior coupling with wedge (1010) at the second end (1048) of actuator arm (1044). Distal translation of applicator actuation mechanism (1018) further acts to compress spring (1032). As applicator arms (1020, 1022) spread apart in opposite outward directions, buttress assemblies (110, 112) may be applied to end effector (12) without requiring any actuation of pivotable anvil (18) or lower jaw (16).

Thereafter, user pressure applied to applicator actuation mechanism (1018) via actuator member (1012) may be released by the user by sliding actuator member (1012) proximally, thereby disengaging from buttress assemblies (110, 112) as buttress assemblies (110, 112) remain adhered to pivotable anvil (18) and lower jaw (16). End effector (12) may thereafter be removed from applicator device (1000).

I. Ninth Exemplary Alternative Applicator Device

FIGS. 23A-23B show a ninth exemplary alternative applicator device (1100) that is configured to apply an adjunct material to a jaw (e.g., lower jaw (16)) of end effector (12) of surgical stapler (10). Applicator device (1100) is configured with the same structures and functionality as applicator device (500, 600, 700, 1000), except for the differences described below. Similarly, application device (1100) includes an applicator actuation mechanism (1102) configured to longitudinally translate relative to cartridge body (1104) to spread applicator arms (1106, 1108) apart from one another and apply one or more buttress assemblies (110, 112) to end effector (12). Applicator device (1100) of this example includes an expansion mechanism in the form of a user-activatable motor (1110). To operate motor (1110) to apply buttresses (110, 112), that is, to extend applicator arms (1106, 1108) of wedge (1112) outwardly, a user may actuate an actuator, such as a press-button (1114) located on cartridge body (1104). To retract applicator arms (1106, 1108), the user may actuate the same actuator (1114) a second time. Optionally, an additional actuator, such as push-button (1116) can be included on cartridge body (1104) to operate motor (1110) in reverse.

J. Tenth Exemplary Alternative Applicator Device

FIGS. 24A-25B show a tenth exemplary alternative applicator device (1200) that is configured to apply an adjunct material to a jaw (e.g., lower jaw (16)) of end effector (12) of surgical stapler (10). Applicator device (1200) is configured with the same structures and functionality as applicator device (500, 600, 700, 1000, 1100), except for the differences described below. Similarly, application device (1200) includes an applicator actuation mechanism (1202) coupled with a platform (1220) configured to longitudinally translate relative to cartridge body (1204) to spread applicator arms (1206, 1208) and apply one or more buttress assemblies (110, 112) to end effector (12).

Applicator device (1200) of this example includes an expansion mechanism in the form of a user-actuatable actuation assembly (1210). To translate applicator actuation mechanism (1210) distally to apply buttresses (110, 112), that is, to extend applicator arms (1206, 1208) of wedge (1212) (i.e., the contact structure) outwardly, a user may manipulate an actuator, such as a squeeze-buttons (1214*a*, 1214*b*) located on cartridge body (1204). As shown in FIGS. 25A and 25B, each squeeze-button (1214*a*, 1214*b*) includes a retaining distal flange (1216*a*, 1216*b*) that is in contact with tabs (1218*a*, 1218*b*) of platform (1220). Further, proximal end (1222) of platform (1220) contacts a compression spring (1224), whereby compression spring (1224) biases platform (1220) toward a distal direction (i.e., toward open end (1226) of cartridge body). As such, as proximal ends (1228*a*, 1228*b*) of actuators (1214*a*, 1214*b*) are squeezed together, distal ends (1230*a*, 1230*b*) of actuators (1214*a*, 1214*b*) translate apart, releasing tabs (1218*a*, 1218*b*) from retaining flanges (1216*a*, 1216*b*). Thereafter, spring (1224) forces platform (1220) and applicator actuation mechanism (1202) distally. As applicator actuation mechanism (1202) and wedge (1212) include the same features as applicator devices (1000, 1100) described herein, applicator arms (1206, 1208) spread apart in opposite outward directions to apply buttress assemblies (110, 112) to end effector (12) without requiring any actuation of pivotable anvil (18) or lower jaw (16). To retract applicator arms (1206, 1208), the user may squeeze distal ends (1230*a*, 1230*b*) of actuators (1214*a*, 1214*b*) to return actuators (1214*a*, 1214*b*) and applicator arms (1206, 1208) to their initial positions as shown in FIGS. 24A and 25A.

K. Eleventh Exemplary Alternative Applicator Device

FIGS. 26A-27B show an eleventh exemplary alternative applicator device (1300) that is configured to apply an adjunct material to a jaw (e.g., lower jaw (16)) of end effector (12) of surgical stapler (10). Applicator device (1300) is configured with the same structures and functionality as applicator device (500, 600, 700, 1000, 1100, 1200), except for the differences described below. Similarly, application device (1300) includes an applicator actuation mechanism (1302) selectively actuatable by a user to spread applicator arms (1306, 1308) of wedge (1312) (i.e., the contact structure of the present version) and apply one or more buttress assemblies (110, 112) to end effector (12). Applicator device (1300) further includes an expansion mechanism defined collectively by an actuator member (1310), applicator actuation mechanism (1302), and applicator arms (1306, 1308), the expansion mechanism selectively operable to transition wedge (1312) between non-expanded and expanded states as explained in greater detail below. Actuation assembly (1310) is configured to be selectively rotated about the longitudinal axis (1304) by a user, and is further configured to couple with applicator actuation mechanism (1302) to thereby rotate applicator actuation mechanism (1302) about longitudinal axis (1304). Applicator actuation mechanism (1302) is formed into an elongate shape, for example an oval shape as shown in FIGS. 27A-27B. Applicator actuation mechanism (1302) is disposed between applicator arms (1306, 1308) and configured to contact and apply radial outward force to applicator arms (1306, 1308) relative to longitudinal axis (1304) upon rotation of applicator actuation mechanism (1302) about longitudinal axis (1304). While an oval shape is illustrated, it has been envisioned that various alternative elongate applicator actuation mechanism (1302) shapes may be utilized.

As shown in FIGS. 26A and 27A, elongate sides (1316*a*, 1316*b*) of applicator actuation mechanism (1302) are rotated to an initial position (i.e., prior to extending applicator arms (1306, 1308)) to contact applicator arms (1306, 1308). A user may grip and rotate actuation assembly (1310) located on cartridge body (1314) 90-degrees about longitudinal axis (1304), as shown in FIGS. 26B and 27B, to therefore extend applicator arms (1306, 1308) to apply buttresses (110, 112). As applicator actuation mechanism (1302) rotates, opposing ends (1318*a*, 1318*b*) of applicator actuation mechanism (1302) rotate into contact with applicator arms (1306, 1308) of wedge (1312) to push applicator arms (1306, 1308) apart. In some versions, elongate sides (1316*a*, 1316*b*) of applicator actuation mechanism (1302) can be shortened or lengthened to thereby respectively decrease or increase the separation distance of applicator arms (1306, 1308) in the expanded state, depending on the separation distance of pivotable anvil (18) and lower jaw (16) of end effector (12). To retract applicator arms (1306, 1308), the user may rotate actuation assembly (1310) 90-degrees in either the same or the opposite direction as before to return applicator arms (1306, 1308) to their initial positions as shown in FIGS. 26A and 27A.

L. Twelfth Exemplary Alternative Applicator Device

FIGS. 28A-28B show a twelfth exemplary alternative applicator device (1400) that is configured to apply an adjunct material to a jaw (e.g., lower jaw (16)) of end effector (12) of surgical stapler (10). Applicator device (1400) is configured with the same structures and functionality as applicator device (500, 600, 700, 1000, 1100, 1200, 1300), except for the differences described below. Applicator device (1400) of this example comprises a torsion spring (1402), a dashpot (1406), a latch (1406), and applicator arms (1408, 1410). Applicator arms (1408, 1410) may be formed into a V-shaped wedge that provides a complementary shape to pivotable anvil (18) and lower jaw (16) that is operable to securely attach buttress assemblies (110, 112) to pivotable anvil (18) and lower jaw (16) when applicator arms (1408, 1410) expand apart while positioned between pivotable anvil (18) and lower jaw (16). Applicator arms (1408, 1410) are pivotably coupled together at their proximal ends (1420, 1422), and torsion spring (1402) is disposed adjacent the pivotable coupling at proximal ends (1420, 1422).

Applicator arms (1408, 1410) cooperate to define a contact structure and are each configured to apply adjunct material to end effector (12) of stapling instrument (10). More specifically, upper applicator arm (1408) is configured to accept buttress assembly (110) thereon for application onto pivotable anvil (18), and lower applicator arm (1410) is configured to accept buttress assembly (112) thereon for application on to lower jaw (16). Particularly, buttress assembly (110) is placed onto upper applicator arm (1408) such that upper adhesive layer (116) is facing outwardly away from upper applicator arm (1408), and buttress assembly (112) is placed onto lower applicator arm (1410) such that lower adhesive layer (120) is facing outwardly away from lower applicator surface (912), thereby allowing first and second adhesive layers (116, 120) to adhere to pivotable anvil (18) and lower jaw (16), respectively, upon application of buttress assemblies (110, 112) by applicator device (900).

FIG. 28A shows applicator arms (1408, 1410) in a non-expanded, pre-application state with buttress assemblies (110, 112) installed thereon. Applicator arms (1408, 1410) are biased to expand in opposite directions by torsion spring (1402). Torsion spring (1402) is disposed at the base of the "V" defined by applicator arms (1408, 1410) and includes spring arms (1412, 1414) extending across inner surfaces (1416, 1418) of applicator arms (1408, 1410), respectively. Applicator arms (1408, 1410) are further coupled together with latch (1406). Latch (1406) is configured to pivotably couple at one end to applicator arm (1410) and include a hook (1420) at the opposing end. In some examples, latch (1406) may instead be configured to pivotably couple at one end to applicator arm (1408). Hook (1420) of latch (1406) is further configured to releasably couple with the other of first applicator arm (1408) or second applicator arm (1410) to prevent applicator arms (1408, 1410) from spreading apart due to the spreading force provided by torsion spring (1402). Torsion spring (1402) and latch (1406) cooperate to define an expansion mechanism configured to be manipulated by a user to transition applicator device (1410) from a non-expanded state (see FIG. 28A) to an expanded state (see FIG. 28B). Additionally, dashpot (1404), or alternatively another similar energy dampening device, is coupled to inner surfaces (1416, 1418) of applicator arms (1408, 1410).

As shown in FIG. 28B, a user may pivot hook (1420) of latch (1406) away from applicator arm (1408), thereby permitting torsion spring (1402) to force applicator arms (1408, 1410) in opposing directions. As described above, spreading applicator arms (1408, 1410) in opposing directions is operable to apply buttress assemblies (110, 112) to end effector (12). As hook (1420) is removed and applicator arms (1408, 1410) spread apart, dashpot (1404) is configured to dampen the rate of spreading motion of applicator arms (1408, 1410). Dashpot (1404) therefore ensures against applicator arms (1408, 1410) spreading too quickly as to cause damage to end effector (12) when applying buttress assemblies (110, 112). End effector (12) may thereafter be removed from applicator device (900).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus configured to apply an adjunct material to at least one of a first stapling surface or a second stapling surface defined by an end effector of a surgical stapler, wherein the first stapling surface includes a plurality of staple apertures and the second stapling surface includes a plurality of staple forming pockets, the apparatus comprising: (a) a contact structure defining a longitudinal axis, wherein the contact structure includes: (i) a first contact member, wherein the first contact member is configured to support a first portion of the adjunct material, and (ii) a second contact member movably coupled with the first contact member, wherein the second contact member is configured to support a second portion of the adjunct material, wherein the first and second contact members are configured to move away from one another in opposing directions toward the first and second stapling surfaces, respectively, to provide the contact structure in an expanded state to apply the first portion of the adjunct material to the first stapling surface with the first contact member and the second portion of the adjunct material to the second stapling surface with the second contact member; and (b) an expansion mechanism operatively coupled with the contact structure, wherein the expansion mechanism is selectively operable to transition the contact structure from a non-expanded state toward the expanded state.

Example 2

The apparatus of Example 1, wherein each of the first and second contact members includes a distal end and a proximal end relative to the longitudinal axis, wherein the proximal end of the first contact member is coupled with the proximal end of the second contact member, wherein the distal end of the first contact member is configured to separate from the distal end of the second contact member while the proximal ends remain coupled together to define a distally opening angle in the expanded state.

Example 3

The apparatus of any of Examples 1-2, wherein the expansion mechanism further includes: (i) a first handle and a first arm coupled with the first handle, wherein the first arm is disposed between the first contact member and the second contact member and is configured to contact the first contact member; (ii) a second handle and a second arm coupled with the second handle, wherein the first arm is disposed between the first contact member and the second contact member and configured to contact the second contact member, wherein the first and second handles are configured to be gripped by a hand of a user; and (iii) a pivot member disposed between the first arm and the second arm, wherein the first and second handles are configured to pivot relative to each other to thereby pivot the first arm relative to the second arm via the pivot member, wherein the first and second arms are configured to force the first and second contact members in opposing directions toward the first and second stapling surfaces.

Example 4

The apparatus of Example 3, wherein at least one of the first arm or the second arm includes a breakaway feature, wherein the breakaway feature in configured to break the at least one of the first arm and the second arm upon an application of force applied to the at least one of the first arm and the second arm which exceeds a predetermined level.

Example 5

The apparatus of any of Examples 1-4, further including a fluid input port in fluid communication with the contact structure, wherein the fluid input port is configured to receive a fluid communicated therethrough, wherein the fluid is operable to actuate the contact structure between the non-expanded state and the expanded state.

Example 6

The apparatus of Example 5, wherein the fluid is comprised of a liquid or a gas, wherein the expansion mechanism comprises a flexible fluid pump configured to couple with the fluid input port, wherein the flexible fluid pump is selectively actuatable to communicate the liquid or gas through the fluid input port.

Example 7

The apparatus of Example 5, wherein the fluid is comprised of a liquid, wherein the expansion mechanism comprises a syringe configured to couple with the fluid input port, wherein the syringe is selectively actuatable to communicate the liquid through the fluid input port.

Example 8

The apparatus of Example 5, wherein the fluid is comprised of a compressed air, wherein the expansion mechanism comprises a compressed air canister configured to couple with the fluid input port, wherein the compressed air canister is selectively puncturable to communicate the compressed air through the fluid input port.

Example 9

The apparatus of any of Examples 1-8, wherein the expansion mechanism includes a rotary actuator, wherein the rotary actuator is rotatable about an axis parallel to the longitudinal axis.

Example 10

The apparatus of any of Examples 1-9, wherein the contact structure includes a compressible foam, wherein the expansion mechanism includes a retainer clip configured to engage the first contact member and the second contact member, wherein the retainer clip is configured to longitudinally translate to disengage the first contact member and the second contact member to thereby permit expansion of the compressible foam and resulting expansion of the contact structure toward the expanded state.

Example 11

The apparatus of any of Examples 1-10, wherein the expansion mechanism includes a user actuation feature, wherein the user actuation feature is configured to slide longitudinally parallel to the longitudinal axis to thereby actuate the contact structure toward the expanded state.

Example 12

The apparatus of any of Examples 1-11, wherein the expansion mechanism includes a motor, wherein the motor is configured to activate to thereby actuate the contact structure toward the expanded state.

Example 13

The apparatus of any of Examples 1-12, wherein the expansion mechanism includes first and second user actuation features, wherein the first and second user actuation features are each configured to receive a force in a direction perpendicular to the longitudinal axis to thereby actuate the contact structure toward the expanded state.

Example 14

The apparatus of any of Examples 1-13, wherein the expansion mechanism includes a user actuation feature, wherein the user actuation feature is configured to rotate about the longitudinal axis to thereby actuate the contact structure toward the expanded state.

Example 15

The apparatus of any of Examples 1-14, wherein the expansion mechanism includes: (i) a latch configured to pivotably couple with one of the first contact member or the second contact member, wherein the latch is configured to engage the other of the first contact member or the second contact member to inhibit the first contact member from separating away from the second contact member, wherein the latch is configured to pivot to disengage the other of the first contact member or the second contact member and thereby permit the first and second contact members to separate, and (ii) a torsion spring disposed between and configured to contact the first contact member and the second contact member, wherein the torsion spring is configured to bias the first contact member away from the second contact member.

Example 16

A surgical instrument assembly, comprising: (a) a surgical stapler end effector including a first stapling surface having a plurality of staple apertures and a second stapling surface having a plurality of staple forming pockets; and (b) the apparatus of any of Examples 1-15, wherein the apparatus is operable to apply the adjunct material to the first and second stapling surfaces.

Example 17

An apparatus configured to apply an adjunct material to at least one of a first stapling surface or a second stapling surface defined by an end effector of a surgical instrument, wherein the first stapling surface includes a plurality of staple apertures and the second stapling surface includes a plurality of staple forming pockets, the apparatus comprising: a wedge defining a longitudinal axis, the wedge including: (a) a first contact member, wherein the first contact member is configured to contact a first portion of the adjunct material; and (b) a second contact member that is configured to move relative to the first contact member to contact a second portion of the adjunct material, wherein each of the first and second contact members includes a distal end and a proximal end relative to the longitudinal axis, wherein the distal end of the first contact member is pivotably coupled with the distal end of the second contact member, wherein the proximal end of the first contact member is configured to selectively pivot away from the proximal end of the second contact member to apply the first and second portions of the adjunct material to a first stapling surface and a second stapling surface of a surgical instrument.

Example 18

The apparatus of Example 17, wherein at least one of the first contact member or the second contact member is configured to secure at least one of the first portion of the adjunct material to the first stapling surface or the second portion of the adjunct material to the second stapling surface.

Example 19

A method of applying an adjunct material to a surgical stapler end effector with an apparatus having a first contact member and a second contact member movably coupled together, wherein the surgical stapler end effector includes a first stapling surface having a plurality of staple apertures and a second stapling surface having a plurality of staple forming pockets, the method comprising: (a) while the apparatus is in a non-expanded state and the end effector is in an open state, positioning the apparatus between the first stapling surface and the second stapling surface such that the first contact member confronts the first stapling surface and the second contact member confronts the second stapling surface; (b) transitioning the apparatus from the non-expanded state to an expanded state to move the first contact member away from the second contact member in a direction toward the first stapling surface; and (c) with the apparatus in the expanded state, securing a first portion of the adjunct material to the first stapling surface with the first contact member.

Example 20

The method of Example 19, further comprising: with the apparatus in the expanded state, securing a second portion of the adjunct material to the second stapling surface with the second contact member.

V. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/022,186, entitled "Apparatus and Method to Apply Buttress to End Effector of Surgical Stapler via Fixed Base," filed on Sep. 16, 2020, published as U.S. Pub. No. 2022/0079592 on Mar. 17, 2022; U.S. patent application Ser. No. 17/022,214, entitled "Apparatus and Method to Apply Buttresses Separately to Jaws of End Effector of Surgical Stapler," filed on Sep. 16, 2020, published as U.S. Pub. No. 2022/0079581 on Mar. 17, 2022, issued as U.S. Pat. No. 11,452,523 on Sep. 27, 2022; U.S. patent application Ser. No. 17/022,414, entitled "Apparatus and Method to Close End Effector of Surgical Stapler onto Buttress," filed on Sep. 16, 2020, published as U.S. Pub. No. 2022/0079583 on Mar. 17, 2022, issued as U.S. Pat No. 11,419,605 on Aug. 23, 2022; U.S. patent application Ser. No. 17/022,419, entitled "Apparatus and Method to Detect Full Seating of Buttress Applicator in End Effector of Surgical Stapler," filed Sep. 16, 2020, published as U.S. Pub. No. 20220079587 on Mar. 17, 2022; U.S. patent appliction Ser. No. 17/022,442, entitled "Apparatus and Method to Apply Buttress to End Effector of Surgical Stapler with Authentication," filed on Sep. 16, 2020published as U.S. Pub. No. 2022/0079584 on Mar. 17, 2022, issued as U.S. Pat. No. 11,413,040 on Aug. 16, 2022; and/or U.S. patent application Ser. No. 17/022,520, entitled "Method of Applying Buttress to End Effector of Surgical Stapler," filed on Sep. 16, 2020, published as U.S. Pub. No. 2022/079593 on Mar. 17, 2022. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus configured to apply an adjunct material to at least one of a first stapling surface or a second stapling surface defined by an end effector of a surgical stapler, wherein the first stapling surface includes a plurality of staple apertures and the second stapling surface includes a plurality of staple forming pockets, the apparatus comprising:
    (a) a contact structure defining a longitudinal axis, wherein the contact structure includes:
        (i) a first contact member, wherein the first contact member is configured to support a first portion of the adjunct material, and
        (ii) a second contact member movably coupled with the first contact member, wherein the second contact member is configured to support a second portion of the adjunct material,
        wherein the first and second contact members are configured to move away from one another in opposing directions toward the first and second stapling surfaces, respectively, to provide the contact structure in an expanded state to apply the first portion of the adjunct material to the first stapling surface with the first contact member and the second portion of the adjunct material to the second stapling surface with the second contact member; and
    (b) an expansion mechanism operatively coupled with the contact structure, wherein the expansion mechanism is selectively operable to transition the contact structure from a non-expanded state toward the expanded state.

2. The apparatus of claim 1, wherein each of the first and second contact members includes a distal end and a proximal end relative to the longitudinal axis, wherein the proximal end of the first contact member is coupled with the proximal end of the second contact member, wherein the distal end of the first contact member is configured to separate from the distal end of the second contact member while the proximal ends remain coupled together to define a distally opening angle in the expanded state.

3. The apparatus of claim 1, wherein the expansion mechanism further includes:
    (i) a first handle and a first arm coupled with the first handle, wherein the first arm is disposed between the first contact member and the second contact member and is configured to contact the first contact member;
    (ii) a second handle and a second arm coupled with the second handle, wherein the first arm is disposed between the first contact member and the second contact member and configured to contact the second contact member, wherein the first and second handles are configured to be gripped by a hand of a user; and
    (iii) a pivot member disposed between the first arm and the second arm,
    wherein the first and second handles are configured to pivot relative to each other to thereby pivot the first arm relative to the second arm via the pivot member, wherein the first and second arms are configured to force the first and second contact members in opposing directions toward the first and second stapling surfaces.

4. The apparatus of claim 3, wherein at least one of the first arm or the second arm includes a breakaway feature, wherein the breakaway feature in configured to break the at least one of the first arm and the second arm upon an application of force applied to the at least one of the first arm and the second arm which exceeds a predetermined level.

5. The apparatus of claim 1, further including a fluid input port in fluid communication with the contact structure, wherein the fluid input port is configured to receive a fluid communicated therethrough, wherein the fluid is operable to actuate the contact structure between the non-expanded state and the expanded state.

6. The apparatus of claim 5, wherein the fluid is comprised of a liquid or a gas, wherein the expansion mechanism comprises a flexible fluid pump configured to couple with the fluid input port, wherein the flexible fluid pump is selectively actuatable to communicate the liquid or gas through the fluid input port.

7. The apparatus of claim 5, wherein the fluid is comprised of a liquid, wherein the expansion mechanism comprises a syringe configured to couple with the fluid input port, wherein the syringe is selectively actuatable to communicate the liquid through the fluid input port.

8. The apparatus of claim 5, wherein the fluid is comprised of a compressed air, wherein the expansion mechanism comprises a compressed air canister configured to couple with the fluid input port, wherein the compressed air canister is selectively puncturable to communicate the compressed air through the fluid input port.

9. The apparatus of claim 1, wherein the expansion mechanism includes a rotary actuator, wherein the rotary actuator is rotatable about an axis parallel to the longitudinal axis.

10. The apparatus of claim 1, wherein the contact structure includes a compressible foam, wherein the expansion mechanism includes a retainer clip configured to engage the first contact member and the second contact member, wherein the retainer clip is configured to longitudinally translate to disengage the first contact member and the second contact member to thereby permit expansion of the compressible foam and resulting expansion of the contact structure toward the expanded state.

11. The apparatus of claim 1, wherein the expansion mechanism includes a user actuation feature, wherein the user actuation feature is configured to slide longitudinally parallel to the longitudinal axis to thereby actuate the contact structure toward the expanded state.

12. The apparatus of claim 1, wherein the expansion mechanism includes a motor, wherein the motor is configured to activate to thereby actuate the contact structure toward the expanded state.

13. The apparatus of claim 1, wherein the expansion mechanism includes first and second user actuation features, wherein the first and second user actuation features are each configured to receive a force in a direction perpendicular to the longitudinal axis to thereby actuate the contact structure toward the expanded state.

14. The apparatus of claim 1, wherein the expansion mechanism includes a user actuation feature, wherein the user actuation feature is configured to rotate about the longitudinal axis to thereby actuate the contact structure toward the expanded state.

15. The apparatus of claim 1, wherein the expansion mechanism includes:
  (i) a latch configured to pivotably couple with one of the first contact member or the second contact member, wherein the latch is configured to engage the other of the first contact member or the second contact member to inhibit the first contact member from separating away from the second contact member, wherein the latch is configured to pivot to disengage the other of the first contact member or the second contact member and thereby permit the first and second contact members to separate, and
  (ii) a torsion spring disposed between and configured to contact the first contact member and the second contact member, wherein the torsion spring is configured to bias the first contact member away from the second contact member.

16. A surgical instrument assembly, comprising:
  (a) a surgical stapler end effector including a first stapling surface having a plurality of staple apertures and a second stapling surface having a plurality of staple forming pockets; and
  (b) the apparatus of claim 1, wherein the apparatus is operable to apply the adjunct material to the first and second stapling surfaces.

17. An apparatus configured to apply an adjunct material to at least one of a first stapling surface or a second stapling surface defined by an end effector of a surgical instrument, wherein the first stapling surface includes a plurality of staple apertures and the second stapling surface includes a plurality of staple forming pockets, the apparatus comprising:
  a wedge defining a longitudinal axis, the wedge including:
    (a) a first contact member, wherein the first contact member is configured to contact a first portion of the adjunct material, and
    (b) a second contact member that is configured to move relative to the first contact member to contact a second portion of the adjunct material, wherein each of the first and second contact members includes a distal end and a proximal end relative to the longitudinal axis, wherein the distal end of the first contact member is pivotably coupled with the distal end of the second contact member,
  wherein the proximal end of the first contact member is configured to selectively pivot away from the proximal end of the second contact member to apply the first and second portions of the adjunct material to a first stapling surface and a second stapling surface of a surgical instrument.

18. The apparatus of claim 17, wherein at least one of the first contact member or the second contact member is configured to secure at least one of the first portion of the adjunct material to the first stapling surface or the second portion of the adjunct material to the second stapling surface.

19. A method of applying an adjunct material to a surgical stapler end effector with an apparatus having a first contact member and a second contact member movably coupled together, wherein the surgical stapler end effector includes a first stapling surface having a plurality of staple apertures and a second stapling surface having a plurality of staple forming pockets, the method comprising:
  (a) while the apparatus is in a non-expanded state and the end effector is in an open state, positioning the apparatus between the first stapling surface and the second stapling surface such that the first contact member confronts the first stapling surface and the second contact member confronts the second stapling surface;
  (b) transitioning the apparatus from the non-expanded state to an expanded state to move the first contact member away from the second contact member in a direction toward the first stapling surface; and
  (c) with the apparatus in the expanded state, securing a first portion of the adjunct material to the first stapling surface with the first contact member.

20. The method of claim 19, further comprising:
  with the apparatus in the expanded state, securing a second portion of the adjunct material to the second stapling surface with the second contact member.

* * * * *